United States Patent [19]

Vago

[11] Patent Number: 5,305,737

[45] Date of Patent: Apr. 26, 1994

[54] ULTRASONIC TREATMENT SYSTEM

[75] Inventor: Robert E. Vago, Bettendorf, Iowa

[73] Assignee: Arjo Inc., Morton Grove, Ill.

[21] Appl. No.: 967,670

[22] Filed: Oct. 28, 1992

Related U.S. Application Data

[60] Continuation-in-part of Ser. No. 753,008, Aug. 23, 1991, Pat. No. 5,178,134, which is a continuation-in-part of Ser. No. 726,948, Jul. 8, 1991, abandoned, which is a division of Ser. No. 322,128, Mar. 10, 1989, Pat. No. 5,048,520, which is a continuation-in-part of Ser. No. 175,936, Mar. 30, 1988, Pat. No. 4,492,868.

[51] Int. Cl.$^5$ ............................................. A61H 1/00
[52] U.S. Cl. ....................................................... 601/4
[58] Field of Search ..................... 128/24 AA, 660.03; 604/22

[56] References Cited

U.S. PATENT DOCUMENTS 3,023,611  3/1962  Howry .......................... 128/24 AA
3,481,687  12/1969  Fishman .
3,585,991  6/1971  Balamuth ....................... 128/24 AA

FOREIGN PATENT DOCUMENTS

0286524B1  10/1992  European Pat. Off. .
968609  3/1958  Fed. Rep. of Germany .
3317045  11/1984  Fed. Rep. of Germany .
1-137960  5/1989  Japan .
1484945  9/1977  United Kingdom .

Primary Examiner—William E. Kamm
Assistant Examiner—George Manuel
Attorney, Agent, or Firm—Vincent L. Carney

[57] ABSTRACT

To provide ultrasonic cleaning of inanimate objects, ultrasonic waves in a frequency range of between 15 kilohertz and 10 megahertz are applied to water in a tank with a power density between 15 and 7,000 watts per square centimeter. Asymmetric power waves are applied to avoid instability leading to transient cavitation. To provide ultrasonic treatment of animals, ultrasonic waves in a frequency range of between 15 kilohertz and 500 kilohertz are applied to water in a tub with a power density between 0.1 and 5 watts per square centimeter. The equipment is able to apply ultrasonic waves with at least two power densities in the vicinity of the portion of the animal with one of said power densities being more than 15 watts per square meter for sterilizing the water before the patient enters the tub and the other being less than 15 watts per square meter.

42 Claims, 6 Drawing Sheets

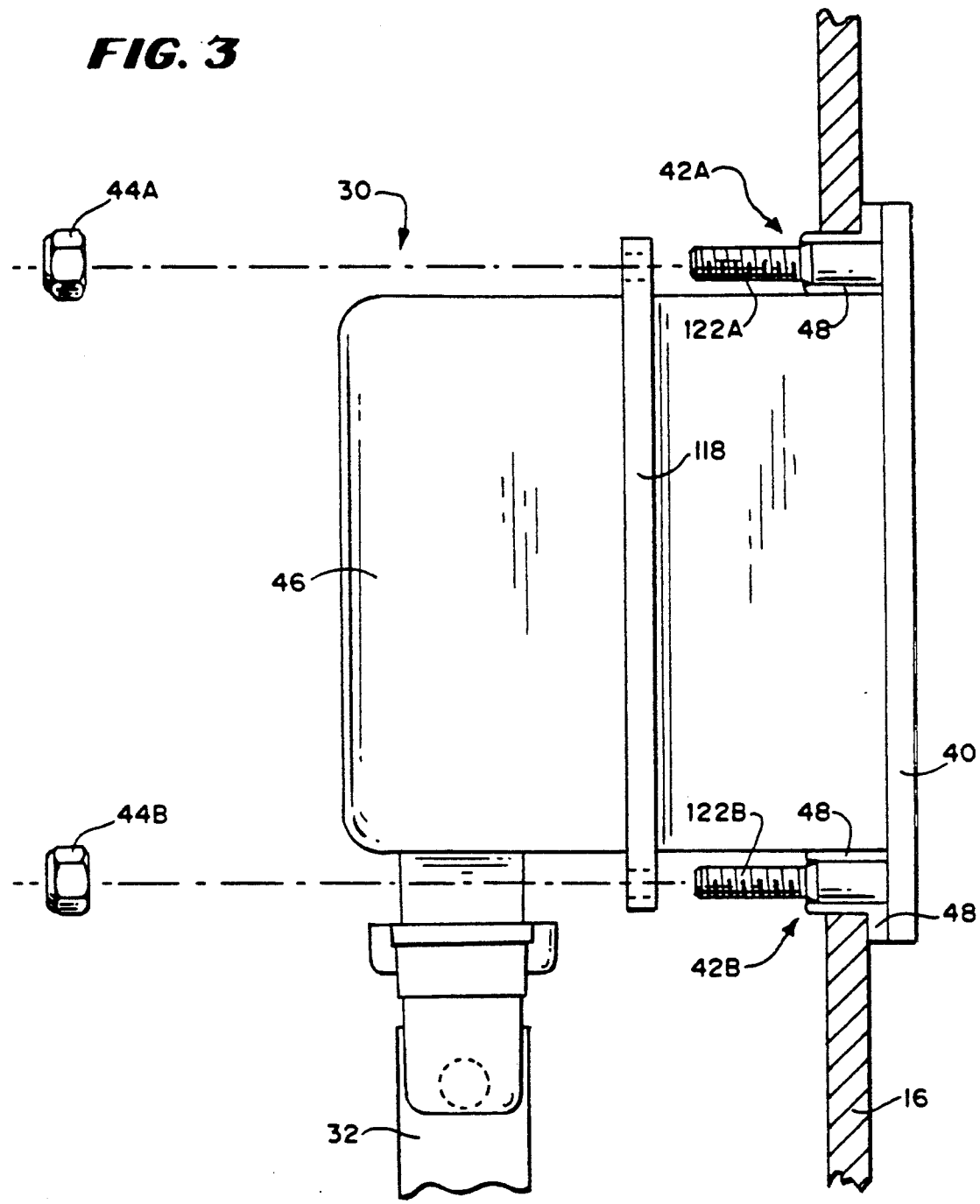

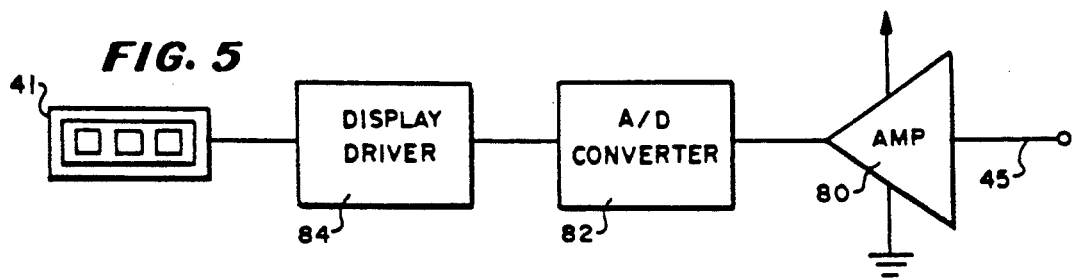
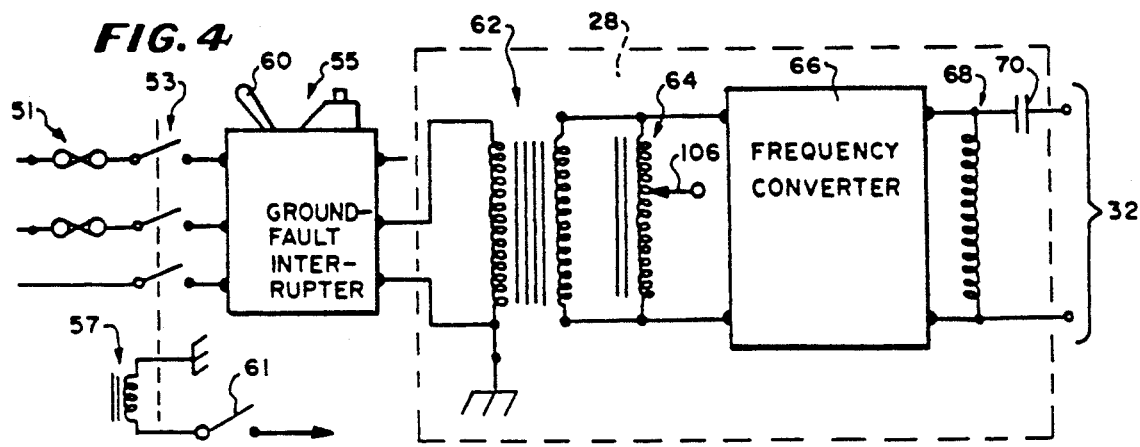
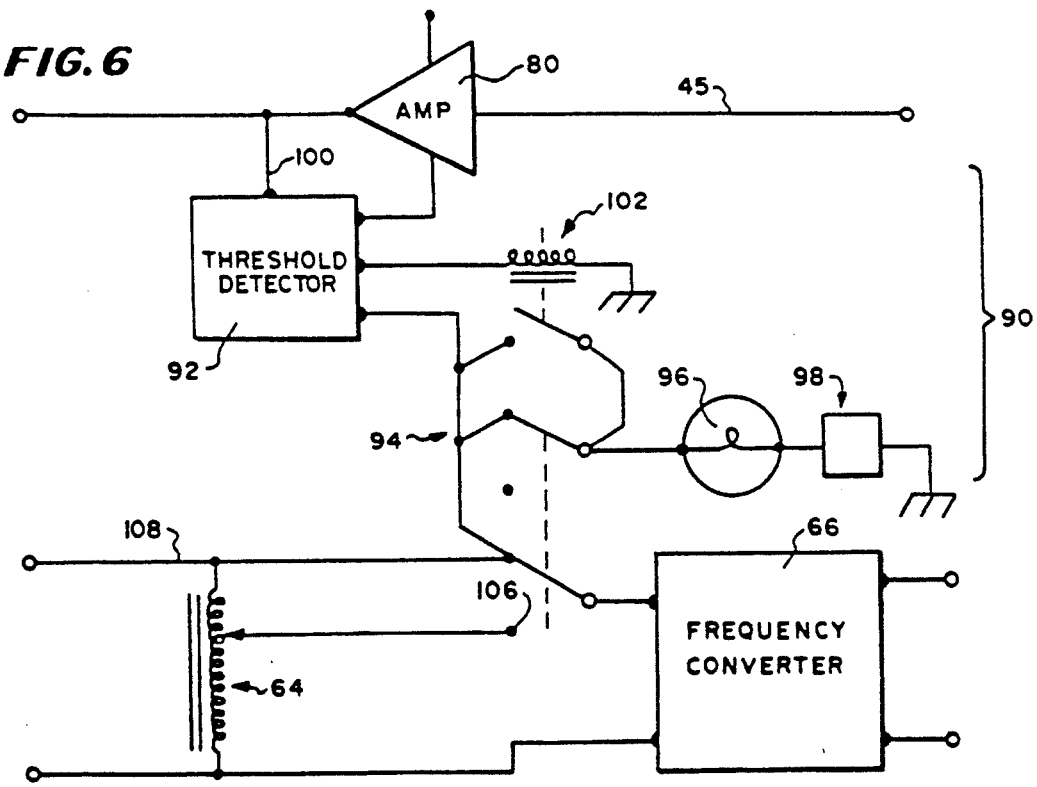

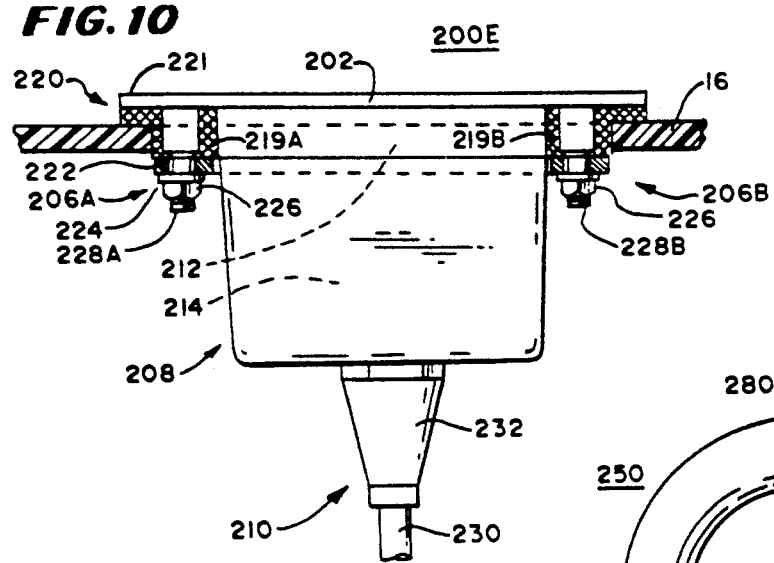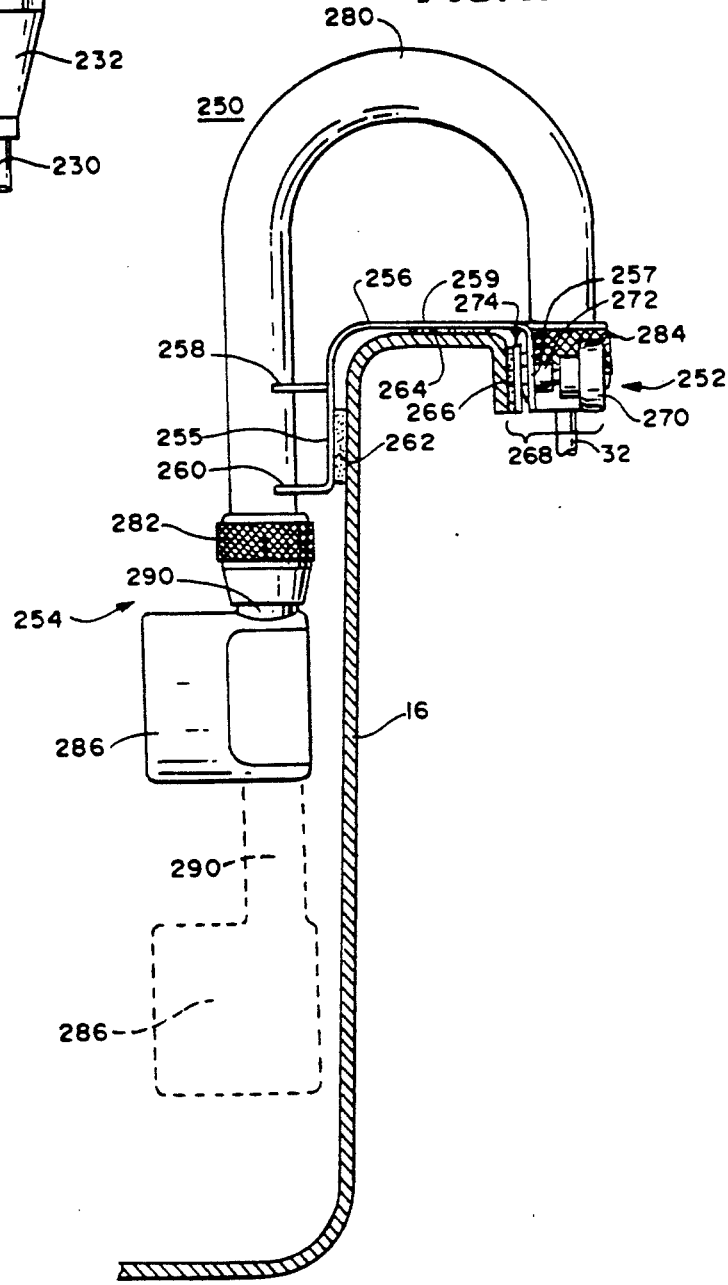

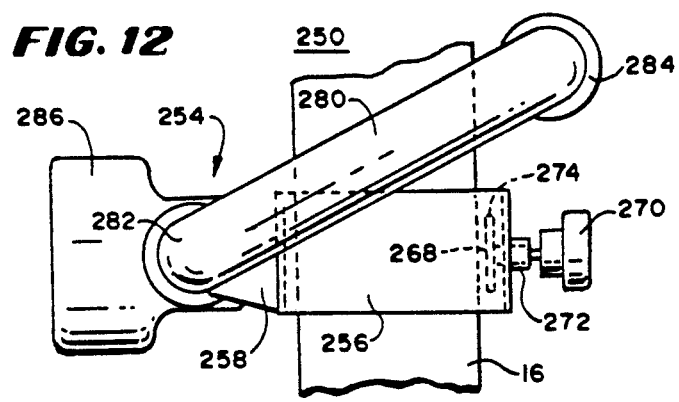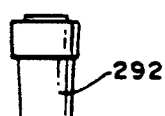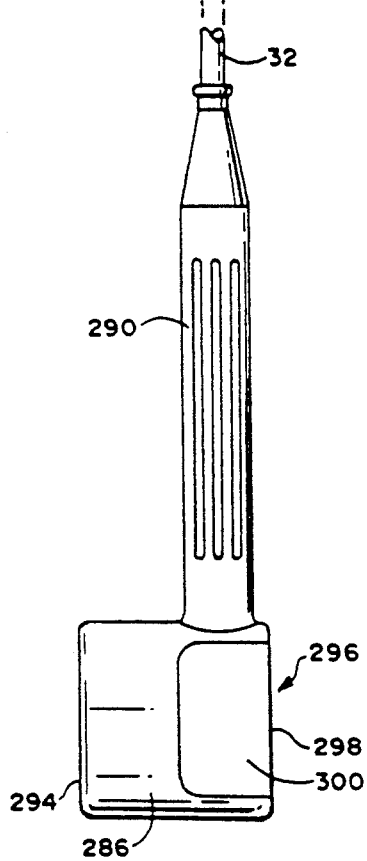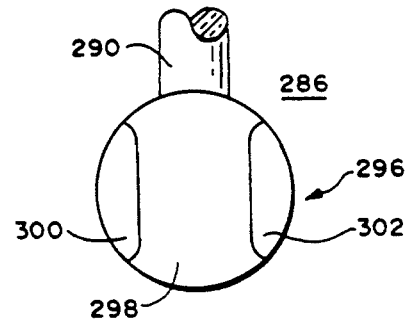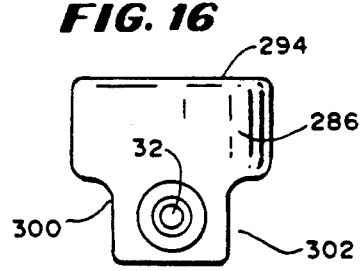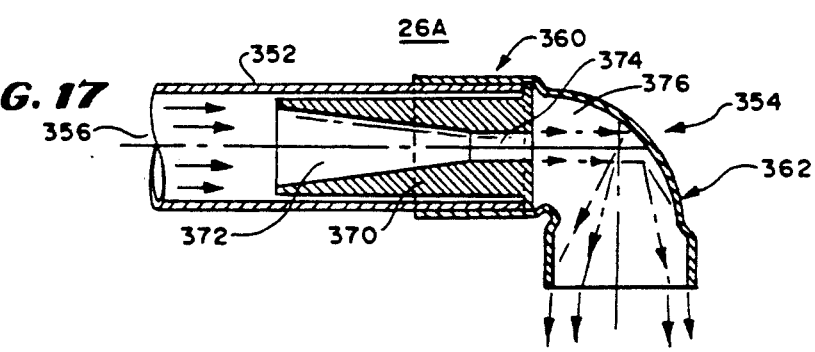

ULTRASONIC TREATMENT SYSTEM

RELATED CASES

This application is a continuation-in-part of application Ser. No. 07/753,008 filed Aug. 23, 1991, now U.S. Pat. No. 5,178,134, which is a continuation-in-part of application Ser. No. 07/726,948 filed Jul. 8, 1991, now abandoned, which is a division of 7/322,128 filed Mar. 10, 1989, now U.S. Pat. No. 5,048,520, which is a continuation-in-part of application Ser. No. 175,936 filed Mar. 30, 1988, now U.S. Pat. No. 4,492,868, in the name of Robert Edward Vago for ULTRASONIC TREATMENT OF ANIMALS and assigned to the same assignee as this application.

BACKGROUND OF THE INVENTION

This invention relates to methods and equipment for ultrasonic treatment such as cleaning inanimate objects and treating animals including humans for purposes of cleaning, hygiene and therapy.

In one class of ultrasonic cleaning and/or treatment, ultrasonic sound is applied to a working fluid by a transducer. The inanimate object or part of the object or part of the animal to be treated is immersed in the working fluid and the transducer transmits vibrations in the ultrasonic range to that animal or object through the working fluid.

In a prior art ultrasonic system of this class, the cleaning tank is made of metal such as stainless steel and an ultrasound generator is epoxy-bonded, bolted or fastened by any other suitable means to a wall. Such prior art ultrasonic systems are most commonly used for cleaning inanimate objects. Stainless steel rather than high percentage carbon steel tanks are employed to effect resistance against chemical corrosion effects which effects are accelerated in the presence of transient cavitation. Cavitation is introduced by large power vibrations resulting in high airborne acoustic noise well over 100 adjusted decibels in a frequency range which is typically between 20 to 60 kilohertz. The applied power is in a range from a few hundred watts to several kilowatts depending on the cleaning application.

In one prior art type of ultrasonic treatment for humans, ultrasonic sound is applied to patients in a range of power levels of from 0 to 5 watts per square centimeter. It is generally used for stiff joints and muscular disorders. Other examples of treatment using ultrasound are provided in U.S. Pat. No. 4,501,151 to Christman, issued Feb. 26, 1985, for ULTRASONIC THERAPY APPLICATOR THAT MEASURES DOSAGE; U.S. Pat. No. 3,499,436 to Balamuth, issued Mar. 10, 1970, for METHOD AND APPARATUS FOR TREATMENT OF ORGANIC STRUCTURES WITH COHERENT ELASTIC ENERGY WAVES; and U.S. Pat. No. 3,867,929 to Joyner, et al., issued Feb. 25, 1975, for ULTRASONIC TREATMENT DEVICE AND METHODS FOR USING THE SAME; and West German Utility model G8714883.8.

The therapeutic treatment described in the prior art has several deficiencies, mainly arising from the failure to use appropriate frequencies and intensities of ultrasound. For example: (1) some frequencies and intensities increase the risk of overheating the underlying tissue of patients; and (2) some are not useable for hygienic purposes because the selected frequency is higher than desirable. Moreover, the prior art literature does not contemplate antiviral, antibacterial or antifungal activity and has not been applied in a manner to accomplish antiviral, antibacterial or antifungal activity in an effective manner.

It is known to clean parts of the body with the aid of ultrasonic waves transmitted through a liquid medium. For example, U.S. Pat. No. 2,970,073 to Prange, issued Jan. 31, 1961, for METHOD FOR ULTRASONIC SURGICAL CLEANING OF HUMAN BODY MEMBERS discloses the use of ultrasonic sound in a range of between 10 to 200 kilocycles per second in a solution of water, germicide and surfactant to cleanse a surgeons hands. This patent recommends powers below 5 watts per square centimeter and frequencies between 15 to 50 kilocycles per second. Still another cleaning apparatus using ultrasound is described in European patent application, publication no. 0049759. This application describes the use of ultrasound and liquid to remove fingernail polish.

In some embodiments of prior art ultrasound cleaning apparatuses, the frequencies are in the megahertz range extending from approximately $\frac{1}{4}$ megahertz to 3 megahertz and in others are above 80 kilocycles such as disclosed in U.S. Pat. No. 3,867,929.

Some ultrasonic cleaning devices of this type have a disadvantage in that they are usable only with additives such as germicides in the case of U.S. Pat. No. 2,970,073 and nailpolish remover in the case of U.S. Pat. No. 3,316,922 or Offenlegungsschrift DE3238476 or European design patent G8714883.8.

The treatment of injured soft tissue and bone is known from Dyson, et al. "Induction of Mast Cell Degranulation in Skin by Ultrasound", *IEEE Transaction on Ultrasonics, Ferroelectronics and Frequency Control,* vol. UFFC 31, n. 2, March 1986, pp. 194–201. However, this information has not been used in an integrated system for bathing and therapy.

Prior art ultrasonic tanks are generally manufactured from stainless steel. Ultrasonic transducers whether they are piezoelectric or magnetostrictive are bonded to the bottom and/or sides of these stainless steel tubs. Stainless steel rather than high percentage carbon steel tubs are employed to effect resistance against chemical corrosion effects, which effects are accelerated in the presence of transient cavitation.

Decoupled transducers have been employed in stainless steel cleaning tanks. For example U.S. Pat. No. 3,301,535 issued to G. G. Brown, entitled "Ultrasonic Washing Machine and Transducer Therefore" discloses the decoupling of transducers with "O" rings that mount magnetostrictive transducers within holes in an ultrasonic cleaning tank for inanimate objects but the problems associated with tank sealing against the egress of the aqueous medium contained within the cleaning tank and the higher incipient manufacturing cost of the decoupled transducer appear to have mandated against their trade usage.

The method disclosed in U.S. Pat. No. 3,301,535, to form a liquid-tight seal between the decoupled transducer and tank, has two disadvantages, which are: (1) the cost of the decoupled transducer construction is inherently higher than a coupled transducer; and (2) the transducer decoupling factor is lowered significantly because the elastomeric vibration isolation medium is compressed to prevent aqueous medium leakage.

SUMMARY OF THE INVENTION

Accordingly, it is an object of the invention to provide a novel apparatus for ultrasonic cleaning.

It is a further object of the invention to provide a novel method for ultrasonic cleaning.

It is a still further object of the invention to provide a novel technique for cleaning with ultrasonic waves which does not damage objects or the container.

It is a still further object of the invention to provide a novel apparatus for ultrasonic treatment of animals.

It is a still further object of the invention to provide a novel method for ultrasonic treatment of animals.

It is a still further object of the invention to provide a novel technique for treating animals with ultrasonic waves which provide hygienic and therapeutic benefits without being irritating or harmful to the animals.

It is a still further object of this invention to provide a technique and apparatus that reduces interference between ultrasonic waves from different transducers, loss of energy and harmful high intensity energy locations in an ultrasonic washer.

It is a further object of the invention to prevent damage to items being treated with ultrasonic vibrations in a liquid by avoiding transient cavitation.

It is a still further object of the invention to increase the uniformity of energy transmission by ultrasonic waves in a fluid.

In accordance with the above and further objects of the invention, an apparatus for ultrasonic treatment includes a container holding a working liquid and means for generating vibrations in the working liquid in a frequency range and in a power range that: (1) in one embodiment, are not irritating or harmful to animals, including humans, and yet which produce one or more beneficial effects, such as for example, cleaning or antimicrobial or therapeutic effects; and (2) in another embodiment, in a different power range, cleans inanimate objects without damage.

The container in the first embodiment is a bathtub but may be smaller such as for example a small container sufficient to immerse a part of the human body such as a foot. In the second embodiment the container is a tank for cleaning inanimate objects. The frequency range and power are selected together to: (1) avoid transient cavitation that may harm the bather or the item being cleaned; but (2) produce sufficient stable cavitation for cleaning or to destroy certain microbes such as harmful bacteria or fungus on the skin or item being cleaned and in the liquid within the container or to promote healing.

In some embodiments, the stable cavitation is controlled to avoid a tendency to become transient. In such embodiments, the linear cavitation is stabilized by controlling the vibrations applied to the working liquid to compensate for shifts in cavitation that occur even with a stable applied vibration. One way of avoiding such instability is by applying an asymmetric pressure wave.

The frequency that is used is in the range of frequencies between 15 and 500 kilohertz. In a bath, the power density is less than 10 watts per square centimeter, although the cleaning efficiency begins to drop as the frequencies exceed 80 kilohertz and some detectable feeling is obtained from power density over 5 watts per square centimeter. The preferred frequency is substantially 30 kilohertz and the preferred power density (SPTP) for bather exposure is 0.1 to 5.0 watts per square centimeter although variations may be made in the two to provide the desirable beneficial effect while avoiding harm to the bather.

Generally in manufacturing a bath or a tank, the size of the container, the liquid, the frequencies of sound, and the power of transmission are selected to provide the cleaning, therapeutic or microbicidal benefits while avoiding deleterious effects to an animal or person or injury to an item being cleaned. Although these factors are all considered during product design and use, the order of selection is generally: (1) the size of the container in connection with the purpose such as for a foot bath or for full bathing of a human or the size of the item; (2) the nature of the liquid, such as degassed water, water with a mild detergent or with a mild antiseptic; (3) the frequency or the sequence of different frequencies to be applied in connection with the purpose; and (4) the power or sequence of powers effective for the desired purpose. After a theoretical selection, the values are adjusted to avoid any observed undesirable effects and maximize benefits. For cleaning, the liquid is generally water and may include a surfactant. The housing of the sound generator and the tank wall are designed to absorb sound and thus reduce acoustical radiation, attenuation or other undesired effects and may be plastic.

Unless special measures are taken, bathers perceive some sound which is not airborne nor generated in the water but is received through the body from the water. This sound, under some circumstances, may be irritating to some users and so it may be desirable under some circumstances to attenuate the sound or alter it in frequency or eliminate it altogether. To alter, attenuate or eliminate the perception of this sound, the vibrating plate or plates may be modified structurally or controlled electrically. They may be modified to reduce the transmission through the water of those subharmonics that may result in the undesirable sound received by the bather. To modify the plates structurally, their shape, their number, their size or the points at which they are driven may be changed. The changes are made to modify the vibrational modes to more suitable modes.

To control the vibrating plates electrically in a way that avoids the perception of sound, the vibrations in the working fluid are sensed by a probe. The sensed vibrations are: (1) processed to remove the principal frequency, which in the preferred embodiment is 30 KHz, such as by filtering; and (2) fed back for control purposes. The sensed lower frequency subharmonics filtered from the sensed vibrations are used to cancel the exciting subharmonics being applied to the working fluid by adjusting the amplitude of the feedback circuit and subtracting the sensed subharmonics from the transducer exciting signal.

For bathing, the liquid is generally water and preferably degassed water with a mild detergent. The housing of the sound generator and the bath container wall are designed to absorb sound and thus reduce acoustical reradiation, or other undesired effects. Precautions are taken to avoid risk of electric shock of a bather.

The ultrasonic vibrations are controlled to compensate for shifts in cavitation that occur even with a stable applied vibration to avoid transients. This is done by applying an asymmetric pressure wave with higher positive pressure than applied negative pressure.

In one embodiment, the tub walls are plastic and a plurality of transducers are each individually inserted through cutouts in the plastic wall of the tank and mounted there by elastomeric decoupling members or elastomeric gaskets. This arrangement provides vibrators that are decoupled from the plastic wall of the tan and decoupled from each other and includes vibrating plates that vibrate directly into the liquid itself.

In another embodiment, a supporting structure permits portability of the transducers. The supporting structure may be removably attached to the tub wall. Adjustable electroconnecting members can move the vibrator to different depths from the edge of the tank and focus it in different directions if needed. A hand held unit ca be used for manual control if desired.

To reduce attenuation and provide uniformity of vibrations throughout the liquid, gas is removed from the liquid and thermal layering of the liquid is reduced. For this purpose any of several techniques may be used. The preferred technique is to apply a slight vacuum to the liquid, followed by an inpact and mixing into the body of water. Another less useful technique is to add a surfactant selected to reduce thermal layering and to reduce bubbles. The surfactant may reduce thermal layering by promoting convection in the liquid and may reduce gas bubbles by reducing the surface tension that holds the bubbles together. The surfactant may also be part of a detergent for cleaning and reducing microbes. Gas bubbles that tend to attenuate ultrasonic vibrations are best reduced by creating vacuum pressure on the water as mentioned previously and thermal layering is best removed by mixing. This may be beneficially done during filling of the cleaning tank.

In the preferred embodiment, gas bubbles are removed by the combination of creating a slight vacuum and impacting the water against a surface. In this embodiment, a jet faucet is used to create the vacuum by increasing the velocity of the water at a narrowed portion of the water faucet and releasing it into a wider portion of the faucet where it hits a wall and drops into the tub. However, a vacuum tank above the liquid or any other such mechanism may be used instead.

To use the ultrasonic treatment for a patient or to clean an item in accordance with the invention, water is degassed, a tub is filled with degassed water and a mild detergent may be added. The item or portion of a patient such as the foot is immersed in the water and ultrasonic sound is transmitted through the water. The sound is transmitted by applying oscillations to a magnetostrictive or piezoelectric transducer which communicates with the water through an electrically insulative vibrating plate in the side of the tub to create vibrations at a selected frequency and power within a frequency range of 15 through 500 kilohertz and preferably at 30 kilohertz with a SPTP power density for patients of less than 15 watts per square centimeter and preferably 0.1 to 5.0 watts per square centimeter and of between 15 watts per square centimeter and 7,000 watts per square centimeter for inanimate objects. In one embodiment, the intensity may be changed to a range between 100 and 20 milliwatts per square centimeter SATA (spatial-average, time-average) in the near field from the transducer.

For safety, a meter measures the power density so observers can determine if it is safe and automatic threshold devices reduce or shut power off should it become too large. Moreover, in some embodiments, a sensor detects a foreign object in the liquid during sterilization and shuts off or reduces the power to prevent harm to the object.

During use by a bather, some germicidal and fungicidal benefits are obtained by the low intensity ultrasound that is safe for the bather. This effect may be synergistically improved with additives that destroy pathogens and are brought into more ready contact with the pathogens by microstreaming induced by ultrasound.

During the inflammation period of wounds, the application of low frequency energy in the range of 15 to 500 kilohertz at intensities of between 1/10 and 5 watts per square centimeter promotes healing. The ultrasound is applied periodically such as for periods of between 5 minutes and 20 minutes at reasonable time intervals such as one or two times each day and results in reduced polymorphs indicating more effective action of the immune system or independent destruction of pathogens. Similarly, during the rapid proliferation healing of wounds, periodic application of this ultrasound in substantially the same ultrasonic frequencies, intensities, time durations and number of repetitions each day promotes FIBROBLAST development.

Because of these effects, it is possible to bathe animals or persons having wounds in a manner that aids in cleaning without damaging the wounds, and under some circumstances, even promoting healing. This is accomplished by immersing a bather with wounds for a number of times between once every two days and four times a day and for a time period selected to avoid increasing inflammation and retarding healing wherein the bather is cleaned while wound healing is aided. The number of times, time durations and repetition rate of bathing with sonically energized working fluid is selected by observing the wounds and optimising the treatment time to secure a lowering of inflammation and reducing the length of time for wound healing.

From the above description, it can be understood that the apparatus and method of this invention has several advantages over the prior art, such as: (1) it has hygienic, therapeutic and antimicrobial benefits while being harmless to animals; (2) it reduces damage to items being cleaned and to the tank itself; (3) it provides a more even transmission of sound; (4) it reduces lost energy; (5) it is economical; (6) it reduces attenuation by degassing with suitable surfactants and efficient vacuum creating devices; (7) it provides flexibility in the use of vibrating transducers by using portable and easily positionable transducers; (8) it reduces transient cavitation by using unsymmetrical sound waveforms; (9) it increases efficiency by providing decoupled transducers; and (10) it performs both cleaning and wound-healing while at the same time providing antiviral, antibacterial and antifungal activity in a manner making it suitable for treatment of certain particularly severe maladies such as severe burns.

DESCRIPTION OF THE DRAWINGS

The above noted and other features of the invention will be better understood from the following detailed description when considered with reference to the accompanying drawings, in which:

FIG. 3 is an elevational, partly-exploded, partly-sectioned, fragmentary view of a transducer element positioned with respect to a container for working fluid in accordance with the invention;

FIG. 4 is a schematic diagram of an ultrasonic generator useful in the embodiment of FIG. 3;

FIG. 5 is a block diagram of a display forming a part of an embodiment of the invention;

FIG. 6 is a schematic circuit diagram of an embodiment of feedback circuit useful in practicing the invention;

FIG. 10 is a fragmentary sectional view of a portion of the embodiment of FIG. 9 taken through lines 10—10;

FIG. 11 is a fragmentary elevational sectional view of a portion of a portable ultrasonic sound controller and generating system;

FIG. 12 is a top view of the embodiment of FIG. 11;

FIG. 13 is a fragmentary view of a portion of the embodiment of FIG. 11;

FIG. 14 is a front view of a portion of the embodiment of FIG. 13;

FIG. 15 is a rear view of a portion of the embodiment of FIG. 14;

FIG. 16 is a sectional view taken through lines 16—16 of FIG. 14; and

FIG. 17 is a sectional view of one embodiment of a gas removal apparatus.

DETAILED DESCRIPTION

Figure 1:
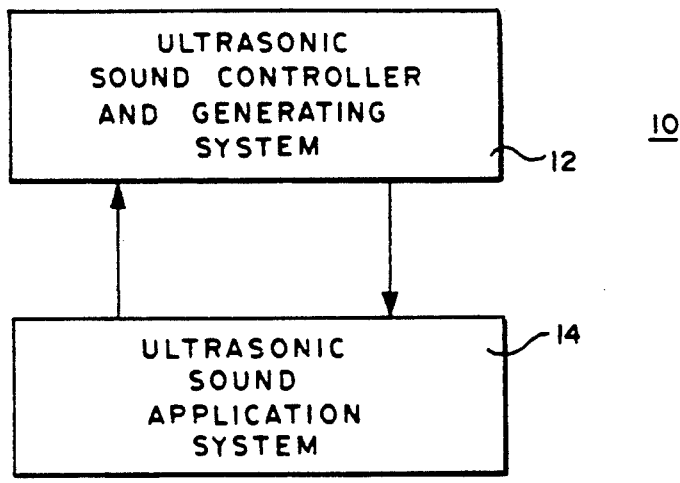
FIG. 1 is a block diagram of an ultrasonic treatment system in accordance with an embodiment of the invention.

In FIG. 1, there is shown a block diagram of an ultrasonic sound system 10 having an ultrasonic sound controller and generating system 12 and an ultrasonic sound application system 14 connected together to supply ultrasonic sound for hygienic, therapeutic and anti-microbial functions or for cleaning. The ultrasonic sound controller and generating system 12 is connected to and transmits signals to the ultrasonic sound application system 14, which may be a bathing system, to provide hygienic and therapeutic benefits to a bather or may be an industrial cleaning tank.

In some embodiments, a transducer within the ultrasonic sound application system 14 supplies a feedback signal to the ultrasonic sound controller and generating system 12 for monitoring purposes The ultrasonic sound system 10 may aid in cleaning, may provide epithelial healing for an animal and particularly for humans and at the same time be actively bacteriocidal, viricidal and fungicidal.

The frequency of the vibrations is maintained in a range within 15 and 500 kilohertz but could be as high as 10 megahertz although this is not a preferred rate and has certain disadvantages. The SPTP power density is less than 15 watts per square centimeter for patients, although the cleaning efficiency begins to drop as the frequencies exceed 80 kilohertz and some detectable feeling is obtained from an SPTP power density over 5 watts per square centimeter. The preferred frequency is substantially 30 kilohertz and the preferred power density is 0.1 to 5.0 watts per square centimeter although variations may be made in the two to provide the desirable beneficial effect while avoiding harm to the bather. The SPTP is between 15 and 7,000 watts per square centimeter for industrial cleaning of inanimate objects.

Energy density (energy per unit area) and intensity (power density or power per unit area) of the ultrasound in this specification is described in terms of spatial-average temporal-average values (SATA), spatial-peak temporal-average values (SPTA), spatial-average temporal-peak values (SATP) or spatial-peak temporal-peak values (SPTP). Of course, these terms have their known meanings in the art so that peak values of energy or intensity are the maximum values occuring in a cycle and energy and power densities are described spatially because they occur at certain areas or temporal to indicate that they occur at a certain time. Similarly, the average values may either be the average values at a given location in given space or the average values at a certain time. In one embodiment, the power intensity is in a range from 100 mW (milliwatts) to 20 mW per square centimeter in the near field from the transducer (SATA).

The frequency and intensity of the ultrasound is selected to avoid tissue damaging heating effects to a bather and damaging heating, pressure and impact effects to an inanimate object being cleaned. By selected frequencies under 500 kilohertz, heat damage to tissue is avoided. Cavitation is the effect which causes beneficial effects and may cause harmful effects.

To avoid harmful effects, cavitation is maintained in a stable range and transient cavitation is avoided because of the risk of damage being done during the collapse of bubbles brought on by the transient cavitation. In stable cavitation, the bubble vibrates at the impressed frequency, growing and shrinking in size between certain size limits.

Because the intensity (power per unit area) varies both with time and space, the transmission of the ultrasound is designed to provide effective operation without damage in all of the regions where the bather or inanimate object may be. Stable cavitation which results in the forming of microstreams of bubbles performs the cleaning operation and under some circumstances may aid in healing and in anti-microbial effects to a bather. In industrial applications such stable cavitation avoids excessive wear and damage to delicate surfaces.

Variations caused by attenuation when a single source of sound is used is reduced by degassing the working fluid or water to remove or avoid large bubbles (larger than 50 microns) which otherwise tend to cause attenuation of the sound as it is transmitted through the working fluid. The preferred degassing method removes or reduces at least air, carbon dioxide and hydrogen sulfide. The smaller voids or bubbles between 20 and 40 microns move back and forth in a process called microstreaming to perform a cleaning operation and to aid in therapy by a stimulation type of activity which reduces the macrophages at wound surfaces. Thus, the lowest SPTP value which occurs adjacent to the bather must be sufficiently high for such microstreaming and the highest intensity (SPTP) must be below that which causes transient cavitation or non-linear cavitation to injure the patient's dermis or under some circumstances damage delicate surfaces and increase wear on objects being cleaned. In industrial cleaning, the higher intensities are obtained by using multiple plates or by pulsing the same transducers and plate to avoid a reduction in efficiency caused by heating effects in the transducer at a high power.

To sterilize the water before bathing, the power density of the ultrasound is increased to a level sufficient to destroy microbes. The ultrasound is applied at a frequency selected for efficiency in destroying the microbes with the lowest power consistent with sterilization and with acceptable levels of sound radiation to the air. This power density SPTP is above 15 watts per square centimeter and at a frequency above 15 kilohertz but may be selected for the circumstances. Additives, such as detergents or antiseptics may be added. This procedure may also be used to sterilize inanimate objects in the liquid. The higher intensity is obtained by using multiple plates or by pulsing the same transducers and plate to avoid a reduction in efficiency caused by heating effects in the transducer at a high power.

Figure 2:
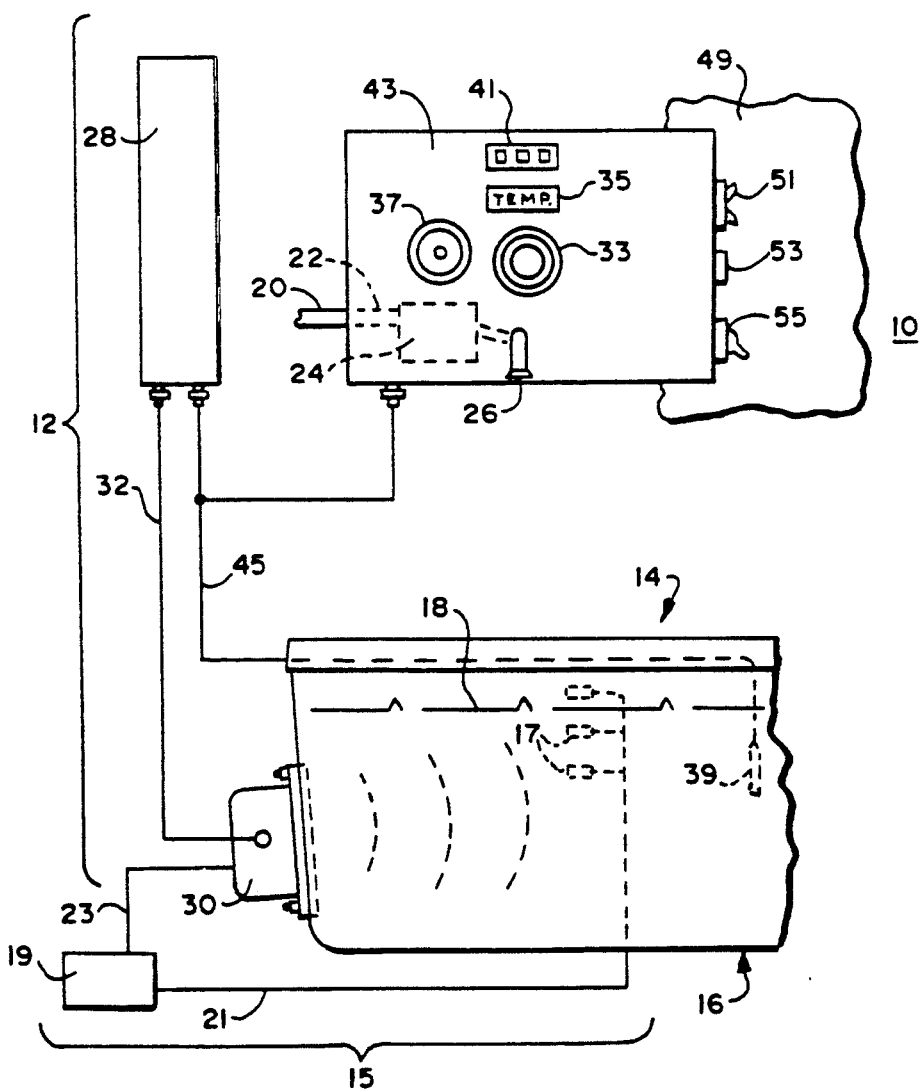
FIG. 2 is a fragmentary schematic diagram of a bathing system which is one form of the ultrasonic treatment system of FIG. 1.

In FIG. 2, there is shown a fragmentary schematic drawing of the ultrasonic system 10 showing one embodiment of ultrasonic sound controller and generating system 12 mounted to one type of ultrasonic sound application system 14. In this embodiment, the ultrasonic sound application system 14 includes a plastic bath tub or industrial cleaning tank 16 containing water as a working fluid 18 and a supply of water such as that available from the faucet 26 in a wall panel 49. In one embodiment, a control system 15 is connected to the bathing system to reduce or terminate high power density ultrasonic waves if a person or other large item accidentally intrudes into the body of water 18 to increase its level to above the planned level. The supply of water 20 is positioned for any preliminary processing necessary and for convenient transfer to the tank or tub 16.

The tub 16 must be sufficiently strong to contain the body of water 18 and sufficiently large so that the objects to be cleaned in an industrial tank may be immersed or in a bathing system a human or other animal such as a pet may have the required portion of its body immersed in the body of water 18. In the preferred embodiment, for patient care the tub 16 is a bathtub but it may be a foot basin or pet bath or the like. For industrial use, the tank must be sufficiently durable to withstand wear from the ultrasonic vibrations to be economical.

To supply working fluid, a supply of fluid includes a pipe or the like 22 to guide the flow of water or other fluid from a convenient source, an additive dispenser 24 and a valve such as a faucet or the like 26 positioned so that water or other working fluid may flow through the pipe 22 from a source, through the additive dispenser 24 and into the tank 16.

The ultrasonic sound controller and generating system 12 includes an ultrasonic generator 28 for generating periodic electric signals and a transducer assembly 30 for converting the electric signals to vibrations that are transmitted through the body of water 18 industrial cleaning of inanimate objects or for cleaning, epithelial therapy and microbicidal effects on animals. The ultrasonic generator 28 receives power from the main power source and may be adapted to utilize either 120 or 220 volt, 60 hertz input power or 50 hertz input power or other voltage levels and frequencies. It is electrically connected by cable to the transducer assembly 30 for supplying vibrations within a frequency range and power suitable for industrial cleaning in one embodiment and in another embodiment for animals a power and frequency that is not irritating or harmful to the patient nor to persons nearby because of sound radiation from the transducer assembly or from water to the air.

The mixture of the liquids flowing from the faucet 26 may be controlled by mixing different proportions of fluids as set by the dial 33 and indicated in the gauge 35.

Similarly, the power density emitted by the transducer assembly 30 is adjustable by the dial 37 and the power of the vibrations in the tank as measured by a transducer 39 is shown on the LED display 41. The temperature of the water can be controlled by mixing cold and hot water.

To apply signals of the selected frequency and intensity to the ultrasound transducer assembly 30, the ultrasonic generator 28 is electrically connected to the ultrasound transducer assembly 30 by a cable 32 and both the ultrasonic generator 28 and control panel 43 are electrically connected to the transducer 39 to receive feedback signals through a cable 45. The control panel 43 also contains other normal electrical devices which are not part of the invention such as an isolation transformer, a ground fault interrupter 51, fuses 53 and a mains power switch 55.

Although in the embodiment of FIG. 2, the transducer 39 is positioned near the expected location of a bather, in the preferred embodiment, a transducer is located in the assembly 30 on an inner plate described hereinafter and connected to the cable 45. The circuit is calibrated at the factory using a transducer located at the expected location of a bather to obtain values corresponding to feedback signals from the transducer on the inner plate.

In some embodiments, a control system 15 includes a plurality of sensors 17 electrically connected to a detector 19 which in turn is connected to the ultrasonic generator 28 for control purposes. The sensors 17 are capacity sensors mounted to the tub 16 to detect an increase in the level of water due to the intrusion of a person or object: into the water. Instead of capacity detectors which detect an increase in the level of the water, other types of detectors may be used including sonic detectors that detect a person near the surface of the water or heat detectors or the like. These detectors supply a signal to the ultrasonic generator 28 when the ultrasonic generator 28 is utilizing high power for sterilization purposes. It is intended to prevent a person from entering the tub while the high power is being applied to avoid harm.

For this purpose, the circuit 19 detects an increase in the level of water as a change in capacitance, differentiates the received signal and applies it to one input of an AND gate. The other input of the AND gate, if energized by the presence of high power signals, de-energizes the ultrasonic generator 28 so that the power is instantaneously eliminated. Instead of terminating the power, a resistance may be inserted in circuit with the electric signal from the ultrasonic generator 28 to reduce the power. These changes occur quickly before harm can be done.

Unless special measures are taken, bathers perceive some sound which is not airborne nor generated in the water but is received through the body from the water. This sound, under some circumstances, may be irritating and should be attenuated, altered in frequency or eliminated.

To alter, attenuate or eliminate the perception of this sound, the vibrating plate or plates may be modified structurally or controlled electrically. They may be modified to reduce the transmission through the water of those subharmonics that may result in the undesirable sound received by the bather. To modify the plates structurally, their shape number or size or points of being driven are changed. The changes are made to modify the vibrational modes to more suitable modes.

To control the vibrating plates electrically in a way that avoids the perception of sound, the vibrations in the working fluid are sensed by a probe. The sensed vibrations are processed to remove the principal frequency, which in the preferred embodiment is 30 KHz, such as by filtering. The sensed lower frequency subharmonics filtered from the sensed vibrations are used to cancel the exciting subharmonics being applied to the working fluid by adjusting the amplitude of the feedback circuit and subtracting the sensed subharmonics from the transducer exciting signal.

To permit power at levels for a sterilization without or with additives, either: (1) special provisions must be made to energize the same transducers used for a bather in a different way; or (2) different or more transducers and vibrating plates may be used. For example, the transducer may be pulsed with high current pulsations to provide spurts of high intensity ultrasound with time between current pulses to permit cooling. In the alternative, multiple vibrations spaced to avoid standing waves can be used.

To stabilize linear cavitation and thus avoid a tendency for the cavitation to become transient, the vibrations applied to the working liquid are controlled in such a way as to compensate for shifts in cavitation that occur even with a stable applied vibration. These shifts occur because the surface area of a bubble is slightly greater during expansion (negative pressure) cycles than compression (positive pressure) cycles. The gas diffusing out of a bubble during a compression cycle is less than the gas diffusing into a bubble during an expansion cycle so that for each successive cycle, the bubble increases in size. Over many cycles (typically 300 microseconds) a bubble can reach resonant size at which it can no longer sustain itself and implodes.

Typically at implosion the temperature of the liquid surrounding the bubble is at 2100 degrees Celsius while the temperature of the vapor within the bubble reaches 5500 degrees Celsius. Correspondingly, the internal pressure can rise to 7500 pounds per square inch, which when in close proximity to the surface, will hurl a water jet towards the surface at 250 MPH. The implosion forces and shock waves not only remove contaminant but also erode surfaces.

One way of avoiding such instability is by applying an asymmetric pressure wave. Since the size increase in a bubble is due to more gas being diffused into a bubble than is diffused out of a bubble, an asymmetric pressure wave having an applied positive pressure higher than the applied negative pressure can equalize the amount of gas diffused into and out of a bubble.

Normally, in ultrasonic cleaning of inanimate objects, a pressure wave of equal positive and negative amplitude is applied to stimulate cavitation because the desired result is normally transient cavitation. However, for the uses described herein, transient cavitation is not desired because transient cavitation events can be damaging to tissue or to delicate surfaces. Instead, an alternative cleaning phenomenon known as microstreaming is created and maintained by stabilizing cavitation. Microstreaming relies upon interaction of thousands of linearly vibrating bubbles for its effect.

In microstreaming, between adjacent stable vibrating bubbles, opposing eddy-currents streams are established in the aqueous medium, and it is these opposing currents which serve to twist the contaminants free of a parent body. This scrubbing action is not violent and represents a virtually non-damaging cleaning mechanism for tissue and for other delicate surfaces.

The asymmetric pressure wave is produced in the ultrasonic sound controller and generating system 12 in a manner to be more fully described hereinafter in connection with FIG. 11. To create and sustain microstreaming, the ultrasonic generator 28 forces the transducer to follow its electrical waveform. Normally, the applied waveform is typically sinusoidal of equal positive and negative amplitude. In the invention, a fixed D.C. bias is added during the positive going wave and subtracted during the negative going wave—positive meaning positive hydrodynamic pressure in the aqueous solution and negative meaning negative hydrodynamic pressure. The fixed D.C. bias is adjustable and may be controlled manually or automatically.

To control the asymmetric pressure wave, the transducer 39 is connected to an oscilloscope to monitor the resulting pressure waveforms. Without transient cavitation being present, the oscilloscope wave outline is clean and free of pertubations. With transient cavitation being present, many spikes appear on the wave outline so when only stable cavitation is present, it is easily determined. This adjustment occurs normally during the factory calibration phase. The D.C. bias control is adjustable either manually or automatically to account for tolerances.

Instead of the analog-to-digital converter 82, the display driver 84 and the LED display 41, an oscilloscope may receive the analog signal and be used to tune the waveform by adjusting the D.C. bias to the ultrasonic generator 28 until no spikes are shown on the display screen of the oscilloscope.

In FIG. 3, there is shown a fragmentary, partly-exploded, partly-sectioned view of an embodiment ultrasound trandsucer assembly 30 electrically connected by the cable 32 to the ultrasonic generator 28 (FIG. 2). The ultrasound transducer assembly 30 includes an interface and a transducer body connected together so that the transducer body generates mechanical vibrations in a selected frequency range and imparts them to the interface which in turn imparts them to the body of water 18 (FIG. 2).

To generate vibrations, the transducer body encloses transducer elements such as those described in U.S. Pat. No. 4,942,868 to Vago issued Jul. 24, 1990, although may other suitable magnetostrictive or piezoelectric transducers are available for use. The transducers are electrically connected to the cable 32 to vibrate in synchronism and thus impart vibrations to the interface. Moreover, an electrically actuated transducer may be positioned near the ultrasonic generator 28 (FIG. 2) and separated from the interface if desirable, with a long acoustic coupling such as a pneumatic coupling being utilized to transfer vibrations to the interface and ultimately to the body of water 18.

To transmit vibrations to the working fluid, the interface includes a vibrating plate 40 and six fasteners 42A–42F, two of which are shown at 42A and 42B, to mount the vibrating plate 40 to the wall 16. In the preferred embodiment, one side of the vibrating plate 40 is mounted to a housing 46 for the ultrasonic transducer assembly 30 and the other side is positioned to be in contact with the body of water 18 in a manner to be described hereinafter.

The six fastener means 42A–42F (only 42A and 42B being shown) include corresponding studs 122A–122F (only 122A and 122B being shown) welded to the vibrating plate 40 and adapted to have threaded upon them corresponding nuts which compress a clamping plate or collar 118 and an annular gasket 48 against the edges of the tank 16 and the housing 46 of the transducer. The main portion of the vibrating plate 0 is on one side of the tank 16 and the transducers on another side s that the vibrating plate 40 is moved by the transducers with respect to the wall of the tank 16 and compresses and decompresses the gasket 48 without permitting fluid to leak therethrough and without acoustic coupling to the wall 16.

To further reduce lost energy and possible irritating or harmful effects, the tank 16 (FIG. 2) is designed to reduce sound transmission to the air and standing waves within the water. As part of this design, the wall of the tank 16 is a sound absorbent plastic material that is particularly absorbent to the frequency of the transducers.

In the preferred embodiment, the plate 40 is generally a 4.25 by 6.25 by three-sixteenth inch rectangular plate but may be of any suitable size. The size of the vibrating plate is determined by the need to transmit sufficient power through the water for the desired purposes such as for cleaning inanimate objects or for hygienic, antimicrobial or therapeutic purposes. However, other materials may be used.

The vibrating plate 40 should be larger than the opening in the tank wall and it directly contacts the body of water 18 (FIG. ). It is sealed to the edge of a corresponding aperture in the tank 16 against escape of the body of water 18 (FIG. 2), with the magnetostrictive vibrator being outside of the tank 16. For this purpose, the elastomeric seal 48 in the circular plate version is a gasket having an open center that contacts the housing 46 outside the tank wall 16 and includes openings for the six studs such as 42A and 42B shown in FIG. 3. The clamping member 118 includes a corresponding six openings and fits over the studs to be compressed against the gasket 48 when the corresponding six nuts, such as those shown at 44A and 44B are tightened over the six corresponding threaded studs 122A-122F, (122A and 122B being shown in FIG. 3). When the clamping collar is forced downwardly it engages the wall 16 and housing 46 to form a liquid tight seal that permits the plate 40 to vibrate but which is decoupled acoustically to some extent from the wall 16.

In FIG. 4, there is shown a schematic circuit diagram of a portion of the ultrasonic generator 28 connected to the ground fault interrupter 55 and fuses 51 through a mains power switch 53. The ground fault interrupter 55 may be of any suitable type containing a manual switch 60 and an internal switch triggered by current to ground of the order of 5 milliamperes to open the circuit. Suitable ground fault interrupters may be purchased from Arrow-Hart, under Model No. 9F2091MI.

The mains power switch 53 may be manually controlled and is, in one embodiment, also controlled by a solenoid 57 to permit it to return to its normally open position when the power density in the ultrasonic sound application system 14 (FIG. 2) exceeds a preset limit in a manner to be described hereinafter.

The ultrasonic generator 28 includes an isolation transformer 62, an autotransformer 64, a frequency converter 66, an output matching inductor 68 and an output isolation capacitor 70. The isolation transformer 62 receives a 120 volts AC on its primary and conducts to the frequency converter 66 a reduced voltage under the control of the autotransformer 64 which may be adjusted to the potential applied to the frequency converter 66.

To generate 30 kilohertz cycles at a power under the control of the autotransformer 64, the frequency converter 66 may be of any suitable type, many of which are available on the market. Suitable frequency converters are sold by Swen Sonic Corp.; P.O. Box 4347, Davenport, Iowa; United States of America. The isolation transformer 62 includes taps to permit either 120 or 230 volt operation in the preferred embodiment for the United States or any other suitable voltages where available. In an embodiment for treatment of patients the frequency converter is a swept frequency generator having a carrier frequency of 30 Khz modulated at 100 or 120 hertz across a band of plus or minus one-half kilohertz for a 1 kilohertz total sweep.

By sweeping the frequency across 1 kilohertz, standing waves are reduced and the sound transmission to air is reduced by eliminating resonance problems. While the modulations are at 100 or 120 hertz in a sweep band of 1 kilohertz, the rate and band may be selected to minimize air borne noise and standing waves. The isolation transformer 62 includes taps to permit either 120 or 240 volt operation in the preferred embodiment.

To minimize noise received by a bather from the water, subharmonic vibrations caused by the sound generator are adjusted until a tolerable sound or no sound is perceived. This may be done by modifying the transducer or vibrating plate or plates to eliminate frequencies more easily perceived when transmitted through the bather's body. Moreover, sounds may be cancelled by transmitting to the bather sounds of the same subharmonic frequencies, such as through the water. This may be conveniently done by sensing the sound in the tub, filtering out the 30 KHz primary ultrasound and feeding the subharmonics back to the vibration plate transducer to cancel the subharmonics. Moreover, by using a much larger sweep in some configurations, noise received by the bather through the bather's body from the water may be reduced.

In FIG. 5, there is shown a block diagram of a circuit for receiving signals from the transducer 39 (FIG. 2) and providing a readout of the power density of the ultrasonic waves on the LED display 41. This circuit includes an amplifier 80, an analog-to-digital converter 82 and a display driver 84. These units by themselves are not part of the invention and one commercial unit is sold under the designations Linear Technology Operational Amplifier LT1014DN.

The operational amplifier is connected to cable 45 to receive signals representing the power density of the ultrasonic frequency, which it smooths and converts to a varying DC signal. Its output is electrically connected to the analog-to-digital converter 82 which converts the DC signal to a digital code for application to the display driver 84, which in turn drives the LED display 41 to indicate the power density in watts per square centimeter of the power of the ultrasonic sound in the body of water 18 (FIG. 2) received by the transducer 39 (FIG. 2). The amplifier 80 has a time constant which results in a DC output from the ultrasonic vibrations representing the total power impinging against the transducer 39 within the water 18 (FIG. 2).

Instead of the analog-to-digital converter 82, the display driver 84 and the LED display 41, an oscilloscope may receive the analog signal and be used to tune the waveform by adjusting the D.C. bias to the ultrasonic generator 28 until no spikes are shown on the display screen of the oscilloscope.

In FIG. 6, there is shown a feedback circuit 90 connected between the output of the amplifier 80 (FIG. 5) and the input to the frequency converter 66 (FIG. 4) to control the power of the ultrasonic vibrations. It includes a threshold detector 92, a three-pole double-throw, relay operated switch 94, a warning lamp 96 and a flasher 98.

To protect against too large a power density, the threshold detector 92 is connected to receive signals from the output of the amplifier 80 through conductor 100 and has a first output electrically connected to the solenoid 102 of the three-pole double-throw, relay operated switch 94. With this connection, the threshold detector 92 energizes the solenoid 102 to throw the three-pole double-throw, relay operated switch 94 from its normal position in which the frequency converter 66 (FIG. 6) receives the full output from the autotransformer 64 shown in FIG. 6 to its energized position in which the frequency converter receives the output from tap 106 of the autotransformer 64 upon the detector 39 (FIG. 2) reaching a SPTP power density greater than a preset power density.

The three-pole double-throw, relay operated switch 94 may be manually set to make contact with tap 106 on the autotransformer 64 to provide a reduced power to the frequency converter 66 for cleaning action or, in the alternative, to its antimicrobial position where the frequency converter 66 is directly connected across the autotransformer 64 at conductor 108 to receive full power. If the power exceeds the predetermined limit in the threshold detector 92, the relay coil 102 is energized to reswitch the three-pole double-throw, relay operated switch 94 back to the autotransformer tap 106, thus reducing power. If the power is not reduced, the threshold detector 92 applies signal to the three-pole double-throw, relay operated switch 94 and the flasher 98 to permit a manual reset of the three-pole double-throw, relay operated switch 94.

Figure 7:
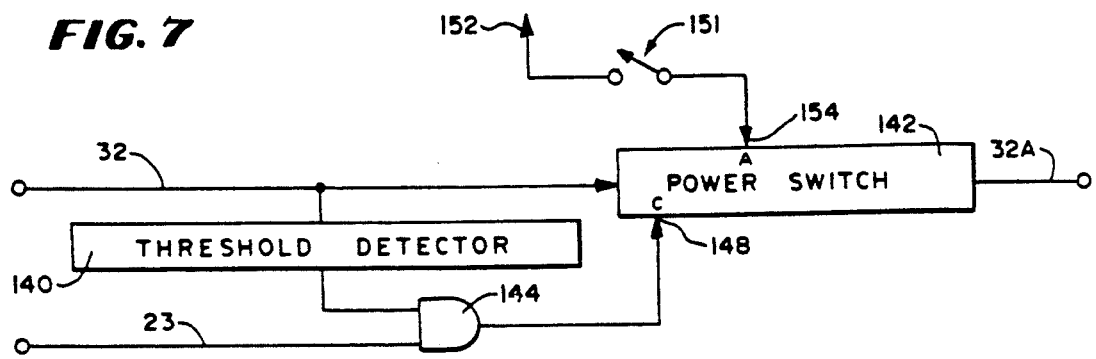
FIG. 7 is a block diagram of a control system which may be part of the cleaning system of FIG. 2.

In FIG. 7 there is shown a block diagram of a circuit suitable for including in the control system 15 in circuit with cable for the purpose of controlling the generation of ultrasonic waves including a threshold detector 140, a power switch 142 and an AND gate 144.

The power switch 142 has its input electrically connected to cable 32 to receive signals from the ultrasonic generator 28 (FIG. 2) and has its output electrically connected to the transducers 132, 134 and 136 (FIGS. 7 and 8) to apply oscillations to the transducers and thus transmit ultrasonic sound through the body of water 18 (FIG. 2). The power switch 142 may be a silicon controlled rectifier circuit, thyratron circuit or relay circuit which is normally closed to permit electrical signals to pass through it but capable of being opened by the application of a signal to a control input 148 and resetable by the application of a signal to a reset input terminal 154. Such circuits are well-known in the art.

To cause the power switch 142 to open, a threshold detector 140 has its input electrically connected to cable 32 and its output electrically connected to one of the inputs of a two-input AND gate 144. The other input of the AND gate 144 is electrically connected to conductor 23 and its output is electrically connected to the control input 148 of the power switch 142.

With this arrangement, when the signal on cable 32 is sufficient to cause ultrasonic vibrations at above 5 watts per square centimeter in the body of water 18 (FIG. 2), the threshold detector 140 applies a signal to one of the two inputs of the AND gate 144. If the body of water 18 now rises so that the sensor 17 (FIG. 2) senses the intrusion of a person into the tub, the detector 19 (FIG. 2) applies a signal through conductor 23 to the other input of the AND gate 144, causing the power switch 142 to receive a signal from the AND gate 144 and open. This terminates the signal to the transducers on cable 32A and thus the oscillations.

The control system 15 may be any type of capacitance detector. Such capacitance detectors are well-known in the field. Moreover, any other type of detector may be used to detect the intrusion or the proximity of an object to the body of water 118.

A reset switch 151 is electrically connected in series with a source of potential 152 and the reset input terminal 154 so that the ultrasound transducer assembly 30 may be reset by closing the reset switch 51 when the bathing system is again ready for operation. With this construction, an additional protection is provided against the accidental insertion into the bath of a person when high power is being applied for sterilization purposes.

Figure 8:
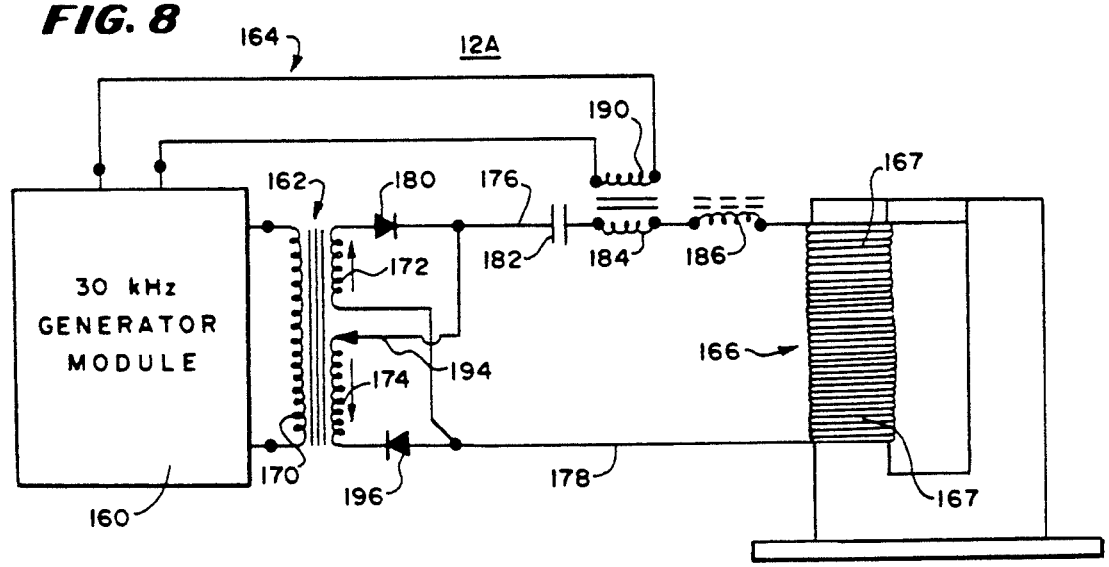
FIG. 8 is a schematic circuit diagram on one embodiment of ultrasonic sound controller and generating system.

In FIG. 8, there is shown an embodiment of ultrasonic sound controlling and generating system 12A having a 30 kilohertz generator module 160, a transformer circuit 162, a transducer 166 and a feedback circuit 164. The transducer 166 is magnetostrictive and is coupled to the 30 kilohertz generator module 160 by the transformer circuit 162 to receive energy to cause vibration. The feedback circuit 164 is coupled to the 30 kHz generator module 160 to maintain amplitude control by feeding back to the 30 kilohertz generator module 160 a signal as negative feedback proportional to the signal applied to the transducer 166.

The transformer circuit 162 includes a primary winding 170 and first and second oppositely-wound secondary windings 172 and 174. The secondary winding 172 has: (1) one end electrically connected through the forward resistance of a diode 180, a conductor 176, a capacitor 182, a primary winding 184 of a feedback transformer and an inductor 186 to a first end of a winding on the magnetostrictive transducer 166; and (2) has its opposite end electrically connected through a conductor 178 to the second end of the winding on the magnetostrictive transducer 166. Similarly, the secondary winding 174 is electrically connected at one end to conductor 176 through an adjustable tap 194 and its other end electrically connected to the cathode of a diode 196, the anode of which is electrically connected to conductor 178.

With this arrangement, the secondary winding 172 transmits current on the positive half-cycle from the 30 kilohertz generator module 160 through the winding 170 to bias the magnetostrictive transducer in a first direction for a positive half-cycle of an ultrasonic wave and the secondary winding 174 transmits current on the negative half-cycles of the 30 kilohertz generator module 160 through the coil 166 to bias the magnetostrictive transducer in a second direction or return direction. The autotransformer 194 may be adjusted to a different induced potential from that transmitted by the secondary winding 172 on the positive going half-cycle so that the ultrasonic wave front transmitted by the transducer is asymmetric and the asymmetry may be adjusted by selecting the tap on the autotransformer.

In the alternative, the secondary winding 174 may be connected to the conductor 176 through a switch with an adjustable resistance to permit adjustable attenuation of the signal on the negative going half-cycle. Moreover, any potential adjustment means may be provided to implement the asymmetric waveform. To provide a signal proportional to the current through conductor 176 back to the 30 kilohertz generator module 160 for amplitude control, the primary winding 154 is coupled to a secondary winding 190 of the feedback circuit 164.

Figure 9:
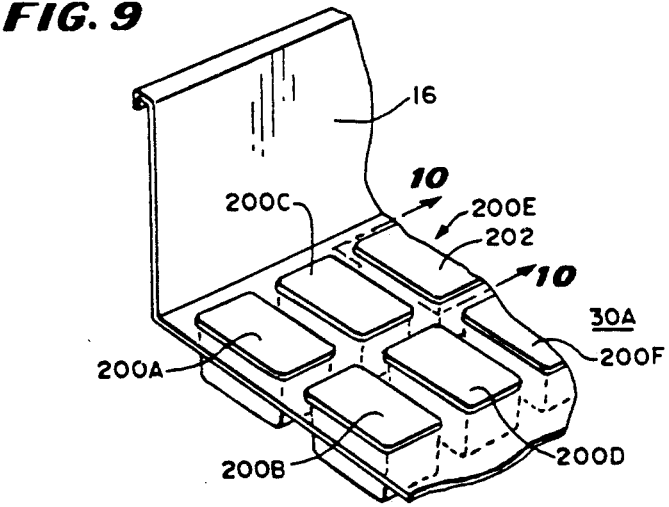
FIG. 9 is a fragmentary perspective view of another embodiment of transducer mounting system.

In FIG. 9, there is shown an array 30A of ultrasonic transducer assemblies 200A-200F mounted to a sound absorbing tub or tank 16 in a fragmentary, simplified, perspective view illustrating four transducer assemblies and two partial assemblies. The tub or tank wall 16 is selected to absorb 30 kilohertz ultrasonic vibrations effectively and contains openings cut in the plastic, each of which receives a specially conforming one of the transducer assemblies 200A-200F which may be dropped in place to be held by a projecting portion of the vibrating diaphram and the gasket of the ultrasonic transducer assembly.

This array, because the transducers are decoupled from the bath or tank and from each other, requires less power, provides accurate feedback of intensity, is low cost and increases the durability of the bath tub or tank itself by reducing the effect of ultrasonic vibrations. The effective ultrasonic vibration is on the bottom wall of the bath tub or tank. The wearing effect of these vibrations is decreased because it is easier to prevent transient cavitation which wears heavily on the bath tub or tank and may damage parts being cleaned in the bath tub or tank. There is better uniformity, less sound emanating from the tub or tank than would be the case with a metal tub or tank and better and safer cleaning and therapeutic action with the same power because of the uniformity within the tank.

In FIG. 10, there is shown a sectional view through lines 10—10 of the transducer array 30A in FIG. 9 having the ultrasonic transducer assembly 200E mounted to the wall 16. As shown in this view, the transducer assembly 200E includes a transducer radiating diaphram 202, two of the six mounting assemblies 206A and 206B, a transducer housing 208, an annular elastomeric gasket 220, an annular clamping plate 222 and the electrical connection assembly 210 connected to a source of ultrasonic electrical signals. The radiating diaphram 202 and the housing 208 are fastened together to form a watertight seal between them such as by molding the edge of the housing to the diaphram. The housing and gasket 220 are sized for a tight fit of the gasket around the housing 208 before the gasket 208 is compressed by the clamping plate 222. With this arrangement, the gasket is expanded outwardly as the backing plate is tightened to fill the space between the tank wall 16 and radiating diaphram sealing.

The transducer housing 208 includes within it a transducer electrically connected to the cabling 210 to cause vibrations of the diaphram 202 within the wall 16 without transmitting those vibrations to the wall 16 or to other transducers to any substantial extent. The radiating diaphram 202 and the transducers within the housing 208 are decoupled acoustically but form a fluid seal with the wall 16 by means of the mounting assemblies 206A, 206B and 206C and 206D (assemblies 206C and 206D not show in FIG. 10).

The transducer housing 208 contains within it the electromagnetic transducers 212 and 214 electromagnetically coupled together with the electromagnetic member 214 being electrically connected to the cabling system 210 to receive electrical ultrasonic vibrations which set up a field that vibrates the electromagnetic member 212. The electromagnetic member 212 is connected to the radiating diaphram 202 to vibrate the diaphram. The electrical connecting assembly 210 includes an electrical input cable 230 which passes through a strain-relief assembly 232 to provide electrical connection to the transducer from the source of ultrasonic vibrations such as the unit 28 (FIGS. 2 and 4).

To mount each of the ultrasonic transducer assemblies such as 200E, a set of six mounting assemblies is provided for each ultrasonic transducer. The manner in which the mounting assemblies cooperate with diaphrams and gaskets to mount their corresponding one of the four ultrasonic transducers will be discussed in connection with the transducer 200E of FIG. 10. Because the mounting assemblies are substantially the same, only the assembly 206A will be described in detail.

The mounting assembly 206A cooperates with the other three mounting assemblies, the gasket 220 and the diaphram 202 to provide a fluid-tight seal. The elastomeric gasket 220: (1) surrounds each assembly; (2) is annular; (3) has bolt receiving portions 219A-219D corresponding to each bolt (219A shown in FIG. 10); and (4) has an outwardly extending annular flange 221 to fit between a corresponding annular outer portion of the diaphram 202 and the top of a portion of the wall 16 surrounding the transducer opening so that it may be compressed between the diaphram 202 and the wall 16 to form a seal.

With this arrangement, an outwardly extending ledge or flange 221 of the gasket 220: (1) is adapted to fit between the wall 16 and the outer portion of the diaphram 202 inside the tank conforming to a portion of the diaphram 202 that extends beyond the housing 208; (2) is tightly gripped around the periphery of the assembly just below the diaphram 202 so that the housing 208 is supported by the diaphram 202; and (3) has a narrowed section which tightly fits within the opening in the wall 16. The diaphram 202 rests on the gasket 220 which conforms to its entire outer periphery.

As best shown in FIG. 10, at least four bolt assemblies fit in corresponding ones of the bolt holding portions 219A-219D and squeeze the diaphram 202 and the wall 16 together to apply pressure on the elastomeric member to cause it to bulge slightly at that location and tightly hold the transducer assembly in place. The mounting assemblies are identical and only one of them, the mounting assembly 206A will be described hereinafter.

The mounting assembly 206A fits within an opening in the annular clamping plate 222 which extends under the elastomeric gasket 220 entirely around the periphery of the assembly. The annular clamping plate 222 may be made of any rigid plastic or metal. It does not engage the wall 16 but only the elastomeric gasket 220. Underneath it is any of a plurality of anti-vibration nuts 224 which are threaded onto corresponding bolts 228A-228D (only 228A and 228B being shown in FIG. 10) which pass through apertures in the bolt receiving portions 219A-219D of the gasket 220, with the top of the bolts being connected such as by welding or brazing to the top of the diaphram 202.

With this arrangement, the electromeric members 212 and 214 vibrate at a frequency driven by signals from the cabling system 210 and thus vibrate the diaphram 202 with the entire unit being separated from the tank wall 16 into which it sits and with which it maintains a liquid-tight relationship.

To further decrease nonuniformity in the intensity of the radiated energy in different location in the tank or tub, active agents such as those included in detergents to reduce the surface tension between different thermal areas in the water or other liquid or surface tension characteristics such as those between air and the liquid are included as an additive. When water is the cleaning substance, a suitable surface active agent is disclosed in U.S. Pat. No. 4,614,612 which is directed to a liquid detergent adapted for dishwashing. In the preferred embodiment, the conditioner formula includes: (1) sodium dodecylbenzene sulfonate, 11.00 percent; (2) sodium lauryl sulfate, 26.50 percent; (3) alkatronic EGE 25 (99 percent polyoxypropylenepoltoxyethylene block polymer; 1 percent preservatives), 25.30 percent; (4) antifoam Dow-Corning 1520 (20 percent polydimethylsiloxane, 70 percent water, 10 percent preservatives), 1.33 percent; (5) urea, 1.83 percent; (6) ethanol, 1.83 percent; (7) citrus, 0.42 percent; and (8) deionized water, 31.79 percent.

Many other surfactants and surfactant combinations are appropriate. The surfactant system must be useful in cleaning, must be compatible with the liquid and should not have such a high density as to interfere with the transmission of ultrasound when dissolved in the appropriate liquid.

In FIG. 11, there is shown a portable ultrasonic transducer assembly 250 mounted to a tank wall 16 with the transducer cable 32 extending from the ultrasonic transducer assembly 250 for connection to a source of ultrasonic electrical signals. The portable ultrasonic transducer assembly 250 includes a tank clamp assembly 252 and a movable transducer housing assembly 254. The tank clamp assembly 252 mounts the movable transducer assembly 254 to the rim of the tank wall 16 and the cable 32 extends into and through the movable transducer housing assembly 254 to provide signals to the transducer. The transducer is mounted within the tank at an adjustable elevation and position by the movable transducer housing assembly 254.

To mount the movable transducer housing assembly 254 to the tank 16, the tank clamp assembly 252 includes an inverted U-shaped bracket 256, two horizontally extending parallel connecting plates 258 and 260, cushioning pads 262, 264 and 266 and a clamp adjustment assembly 268.

The inverted U-shaped bracket 256 is of sufficient size to fit around the bent-over rim of the wall 16 and has a horizontal portion 259 overlying a horizontal portion of the rim and vertical portions extending parallel and spaced from the vertical portions of the wall 16 of the tank. The three pads 262, 264 and 266 are positioned respectively between the first or inner vertical portion 255 of the U-shaped bracket 256, the horizontal portion 259 and the second or outer vertical portion 257 of the U-shaped bracket 256 and the rim of the tank 16 to space the U-shaped bracket 256 from the wall 16.

The first and second vertical connecting plates 258 and 260 are parallel to each other with the lower plate 260 being formed at the end of the first vertical portion 255 of the bracket 256 on the innerside of the tank or tub and welded to the movable transducer housing assembly 254. Similarly the upper connecting plate 258 is welded both to the bracket 256 and the housing assembly 254 so that the two parallel plates 258 and 260 hold the housing assembly 254 to the U-shaped bracket 256.

The clamp adjustment assembly 268 is on the outer side of the inverted U-shaped bracket 256 with the horizontal plates 258 and 260 being on the inside. The clamp exerts pressure between vertically extending portions of the U-shaped clamp 256 and an opposite vertical surface of the wall 16 at its rim to form a firm connection between the ultrasonic transducer assembly 250 and the tank wall 16.

To clamp the U-shaped bracket 256 to the rim of the tank wall 16, the clamp adjustment assembly 268 includes a rotary handle or knob 270, a screw member 272 and a clamping plate 274. In the preferred embodiment shown in FIG. 11, the rim of the wall 16 at its upper end is bent outwardly from the center of the tank to form the horizontal portion and then downwardly. The clamp adjustment assembly 268 grips the end of the tank by pressing between the outermost surface of the tank wall or walls at its upper edge and the adjacent second vertical portion 257. However any of many clamping approaches can be used for this purpose.

To grip the surfaces of the wall 16 at its upper edge, the second or outer vertical portion 257 of the inverted U-shaped bracket 256 includes a tapped hole and a screw includes external threads that are adapted to engage the internal threads on the tapped hole so that the screw passes through the hole. The end of the screw is welded or otherwise connected to the clamping plate 274 on the inner side of the vertical second portion 257 of the bracket 256 to be moved toward and away from the outer vertically downward portion of the wall 16. With this arrangement, pressure is applied between the outer vertical portion 257 and the cushioning pad 266, which pad 266 presses against the wall 16 to clamp the bracket 256 to the wall 16.

The other end of the threaded portion of the screw is connected to the rotary handle 270 so that: (1) clockwise rotation of the handle 270 forces the clamping plate 274 more tightly against the pad by extending the threaded portion of the screw a greater distance between the second downwardly vertical portion 257 of the U-shaped bracket 256 and the side of wall 16 of the tank until the bracket 256 is firmly attached to the wall; and (2) counterclockwise rotation of the handle 270 loosens the clamping plate 274 from the pad by retracting the threaded portion of the screw toward the second downwardly vertical portion 257 of the U-shaped bracket 256 and away from the side of wall 16 of the tank until the bracket is loose and removable from the wall. With this arrangement the movable transducer housing assembly 25 is replaceably mounted to the tank.

The movable transducer housing assembly 254 includes a cable tube 280, first and second collets 282 and 284, a transducer housing 286 and an adjustable housing extension 290. The protective cable tube 280 is cylindrical, having a circular cross-section and a central axis extending along its length shaped as an inverted "U". One leg of the inverted "U" extends vertically downwardly inside of the tank and is welded to the connecting plates 258 and 260 and the other leg extends vertically downwardly outside of the tank wall 16, with the transducer cable 32 extending from outside the tank to inside the tank and being movable within the cable tube 280.

The adjustable housing extension 290 is a vertically extending tube that fits within the inward vertical portion of the cable tube 280 at one end and is connected to the transducer housing 286 at the other end so that it may be moved upwardly and downwardly and tightened in position by the collet 282 to permit the transducer housing 286 to be at different depths within a liquid in the tank 14. In the elevational view of FIG. 11, the housing 286 is shown with the extension 290 entirely within the U-shaped cable tube 280 but also showing in phantom lines, the extension 290 and the housing 286 at a lower depth.

In FIG. 12, there is shown a plan view of the adjustable ultrasonic transducer assembly 250 mounted to the rim of the wall 16 with the transducer housing 286 at its highest elevation where it is clamped in position by the collet 282. As shown in this view, the clamps clamp the U-shaped cable tube 280 to the tank but the collet 282 may be loosened to permit the transducer housing 286 to be pulled to lower depths and pointed at any angle. The collet 282 may be tightened when the transducer housing 286 is in a selected position to hold the transducer housing 286 in the selected position.

In FIG. 13, there is shown an elevational view, partly exploded, of the transducer housing 286, the housing extension 290, the cable 32 and an electrical plug attachment 292 that may be connected to a mains outlet in a wall panel. In this view, the extension 290 is shown connected with the transducer housing 286. The transducer housing 286 has a radiating face 294 and a rear face 296. The rear face 296 has an outward extending portion 298 and two inwardly cutaway portions, one of which is shown at 300 in FIG. 13.

As shown in FIG. 14, the transducer housing 286 includes a radiating face 294 with a central vibrating membrane held within a rim to radiate ultrasonic sound throughout the tub. This radiating face 294 may be stainless steel or glass bonded over metal, but of course a plurality of individually mounted transducers may be used or any other type of radiating surface or surfaces.

In FIG. 15, there is shown the rear end 296 of the transducer housing 286 having a central, slightly extended portion 298 and slightly cutaway portions 300 and 302 with the extended portion 298 receiving the cable 32 (FIG. 13) for connection to the transducers that move the radiating face 294. This is better shown in FIG. 16 showing the radiating face 294 and the housing adjacent to it being of sufficient size to accommodate an electromagnetic ultrasonic vibrator as described in the previous embodiments.

In FIG. 17, there is shown another embodiment of faucet 26A mounted in the same manner as the faucet 26 in FIG. 2 including a connecting pipe 352 and a degasser 354. A connecting tube 356 may be connected to the additive container 24 or to the pipe 22 (FIG. 2) through the connecting pipe 352.

The degasser 354 includes a vacuum portion 360 and an impact portion 362. The vacuum portion 360 includes an insert 370 having a tapered inlet 372 fitting conformably within the connecting pipe 352 to receive substantially all of the liquid flowing therethrough and narrowing to an outlet portion 374, thus increasing the velocity of flow of the liquid. A wider larger-cross-sectional area or release portion 376 permits an expansion of the fluid to create vacuum pressure prior to the liquid hitting the impact portion 362, from which it drops downwardly.

This degasser is principally intended to remove carbon dioxide dissolved in the liquid but may also remove hydrogen sulfide, nitrogen and oxygen. In operation, the vacuum formed by the increased velocity liquid causes small bubbles to form, which are released upon hitting the impact surface 362. The impact surface 362 must be no further removed than two inches from the vacuum area and may be incorporated within the area of vacuum or separated from it.

In the preferred embodiment, the impact surface 362 is within the vacuum at its outer periphery and is part of the downwardly extending portion of the faucet but may be a short distance from the vacuum provided the impact occurs within one minute of depressurizing the liquid. The velocity of the liquid leaving the high velocity portion is at leas six linear inches per minute and the flow rate is at least six cubic centimeters per minute. The release area 376 has a cross-sectional area at least ten percent greater than the cross-sectional area of the adjacent high velocity section to create a vacuum of at least 1/100 of an atmosphere (negative pressure of 1/100 of an atmosphere or 1/100 of an atmosphere below atmospheric pressure).

Before being supplied to an end user, the transducer 39 is calibrated for the actual tub. This is done by measuring the power with a transducer located where the bather is expected to be and with a standard calibrated meter. The amplifier 80 (FIG. 5) is adjusted until the readout 41 (FIGS. 2 and 5) corresponds in its reading to the reading on the standard meter while the cable 45 is connected to the transducer 39A.

In operation for a patient, the operator fills the tub 16 with the body of water 18, adjusts the comfort controls for temperature and type of treatment and, after the patient is in the tub, energizes the arrangement to provide vibrations. The frequency and power density of the vibrations may be set in accordance with the purpose of the unit. For example, cleaning may be performed at a lower power than antimicrobial treatment. The power may be changed during the bathing process so as, for example, to provide microbicidal activity at a first power density before the patient enters the tub and effective cleaning at a lower power density after the patient enters the tub.

To adjust the comfort level, the temperature of the water is controlled by the temperature control 37 (FIG. 2) as water flows from the faucet 26 (FIG. 2) until water has substantially filled the tub 14 or filled it to the desired level for treatment. The power density is then set by adjusting the dial 33 (FIG. 2), which adjusts the autotransformer 64 (FIG. 4).

To begin the treatment, the mains power switch 53 (FIG. 4) is closed which then applies power to the ground fault interrupter 55 and to the isolation transformer 62 so that the frequency converter 66 begins sweeping at its preset frequency, which normally will be 30 kilohertz with a 1 kilohertz sweep frequency. Although the frequency converter in the preferred embodiment is capable of providing up to 500 watts of power, much lower powers are provided. The power is selected to result in the desired power density within the fluid by monitoring the fluid as the power is adjusted by the dial 37 (FIG. 2).

The power is monitored by measuring the power of the vibrations on the transducer 39 (FIG. 2) and transmitting signals representing this power to the amplifier 80 (FIG. 5) which amplifies it and transmits it to the analog-to-digital converter 82 (FIG. 5) which converts it to digital form and transmits it to the LED display 41 (FIG. 5).

To control the power, the dial 37 (FIG. 2) is turned generally until the power is in the range of 0.1 to 5.0 watts per square centimeter as read on the meter. The dial 37 moves the tap on the autotransformer 64 (FIG.

4) to control the voltage applied to the frequency converter 66. The power generated by the ultrasonic generator 28 is applied through the cable 32 to the ultrasound transducer assembly 30 (FIGS. 2, and 6) which results in vibrations being applied through the vibrating plate to the bath where they are applied to the patient and sensed by the transducer 39 (FIG. 2). Generally, the power is applied for fifteen minutes or less: and at a power and frequency which will not result in transient cavitation but yet to perform hygienic, antimicrobial or therapeutic treatment.

During use by a bather, some germicidal and fungicidal benefits are obtained by the low intensity ultrasound that is safe for the bather. This effect may be synergistically improved with additives that destroy pathogens and are brought into more ready contact with the pathogens by microstreaming induced by ultrasound.

During the inflammation period of wounds, the application of low frequency energy in the range of 15 to 500 kilohertz at intensities of between 1/10 and 5 watts per square centimeter promotes healing. The ultrasound is applied periodically such as for periods of between 5 minutes and 20 minutes at reasonable time intervals such as one or two times each day and results in reduced polymorphs indicating more effective action of the immune system or independent destruction of pathogens.

Similarly, during the rapid epithelial healing of wounds, periodic application of this ultrasound in substantially the same ultrasonic frequencies, intensities, time durations and number of repetitions each day promotes fibroblast development.

Because of these effects, it is possible to bathe animals or persons having wounds in a manner that aids in cleaning without damaging the wounds, and under some circumstances, even promoting healing. This is accomplished by immersing a bather with wounds for a number of times between once every two days and four times a day and for a time period selected to avoid increasing inflammation and retarding healing wherein the bather is cleaned while wound healing is aided. The number of times, time durations and repetition rate of bathing with sonically energized working fluid is selected by observing the wounds and reducing time in the ultrasound energized working fluid upon any one of irritation during bathing, increased inflammation after bathing or show healing rate.

If a ground fault is created, the current through the ground connection of the ground fault interrupter 55 (FIG. 4) causes it to open the circuit and terminate operation. Moreover, if the power density in the water 18 exceeds the amount set in the threshold detector 92 (FIG. 6), the relay solenoid 102 opens the circuit containing solenoid coil 57 (FIG. 4) through relay switch 61, causing the normally open mains power switch 53 to open. If this safety circuit fails, three-pole double-throw, relay operated switch 94 energizes warning lamp 96 and flasher 98 to provide an alarm.

In one embodiment, ultrasonic vibrations are applied at a power density of above 30 watts per square centimeter. In this embodiment, an additive is desirable, which may weaken cell walls of microbes or oxidize microbes. The ultrasonic vibrations at high power by themselves may sterilize the water and inanimate objects in it but the combination of additives for cleaning and further antiseptic reasons synergistically sterilize the water and, if desired, may clean and sterilize inanimate objects such as instruments and the like.

A detector in this embodiment detects the presence of a person or other object while the high power is being applied. For example, capacitance detectors may detect any time the water rises in the container. The detection will immediately deenergize or insert an attenuator in circuit with the ultrasonic generator to reduce the power density before damage can be done to a person who may accidentally enter the body of water.

When the water has been sterilized, in some embodiments such as those that are used for bathing or other treatment of animals, the power may be reduced to a level that is not irritating or damaging. The patient or other animal may then enter the bath and be subject to its cleaning action or other beneficial action from the bath without fear of contamination from the water.

One aspect of the invention is illustrated by the following examples:

EXAMPLES

The following examples illustrate the effect of ultrasound at 30 KHz on fungus, bacteria and virus in the absence of additives. The sound was applied to cultures in bags mounted in a tub in accordance with the invention. The power levels were determined according to a calibrated voltage meter as shown in Table 1. Concentrations were calculated according to formula 1.

EXAMPLE 1

Fungus

1. Type: *Trichophyton mentagrophytes*

2. Procedure

*T. mentagrophytes* was grown at 26 degrees Centigrade on Emmon's modification of Sabouraud's agar (25 ml/plate). Agar plugs of one cm in diameter were taken from the fungal culture and transferred to a sterile Whirl-Pak (registered trademark) with 10 ml of sterile phosphate buffer at pH=7.0. After the treatments, the fungal plug was replated on the agar media stated above. One ml (milliliter) of the buffer was plated with the fungal plug to account for the fungal spores which may be lost during the period of time spent in the Whirl-Pak (registered trademark). This procedure was followed for the first experiment but was later modified for the subsequent experiments, whereby the plug was simply blotted on sterile filter paper to deter contaminants carried in the buffer, from being plated with the fungal plug.

TABLE 1

| Meter Setting | I(SPTP) | I(SPTA) | Specimen I(SATA) |
|---|---|---|---|
| 110 V AC | 2.5 W/cm² | 0.2 W/cm² | 0.1 W/cm² |
| 170 V AC | 5.5 W/cm² | 0.4 W/cm² | 0.3 W/cm² |
| 220 V AC | 11.3 W/cm² | 0.5 W/cm² | 0.4 W/cm² |

Initial Concentration = $\frac{\text{\# of colonies}}{\text{vol. plated out.}}$ (x) dilution Formula 1

The plates were then incubated at 26 degrees Centigrade and ranked daily according to the amount of growth shown.

The amount of growth that appeared on plates was ranked in a grading from the least amount of growth to the greatest amount of growth. There were three sources of data to be reported. The exposed samples were those within the field of ultrasound exposure in the tub at 39 degrees Centigrade. Sham samples were placed in the same water (at 39 degrees Centigrade) but were placed beyond a barrier which protected them from exposure to ultrasound. Control samples remained at room temperature and never entered into the water.

3. Results

Experiments suggested that ultrasound affected fungus growth. Two gave inconclusive results. In one experiment of the 15 specimens, all ultrasonic exposures were for a duration of 60 minutes, at either the 170 V AC or 220 V AC meter setting. All six of the exposed samples appeared in the lower growth gradings and all but one of the six shams were graded similarly to those of the three controls which were higher.

In another experiment, four out of the six exposed samples appeared in the two lower growth gradings five out of the six exposed samples appeared in the three lower growth gradings, but one sample that was exposed for 60 minutes at 220 V AC appeared in the grading of substantial growth. In still another experiment, of the twelve exposed samples, seven appeared in the three lowest growth gradings, and nine appeared in the four lowest growth gradings. However, three appeared in the grading of most growth attained.

EXAMPLE 2

Bacteria

1. Types

*Eschericia coli* (*E. coli*)
*Staphylococcus aureus* (*S. aureus*)
*Bacillus subtilis* (*B. subtilis*)
*Pseudomonas fluorescens* (*P. fluorescens*)
*Pseudomonas aeruginosa* (*P. aeruginosa*)

2. Procedure

The procedure used to determine viability (survival capability) of the bacterial cells is the spread plate technique. The principle of the technique is that a certain volume (0.1 ml) of bacteria at a known concentration is pipetted out onto a sterile nutrient agar plate. The plates are incubated at 37 degrees Centigrade for a minimum of 24 hours. Any viable (living) cells grow on the agar into colonies and from these colonies, a concentration of viable cells/ml saline is obtained.

The bacteria remain in the broth until use in the experiment. The procedure is as follows:

The initial concentration is diluted with sterile normal saline. The cultures are diluted to a point where between 30–300 colonies/plate are obtained. This diluting is required in order to assure accurate counts of each colony.

After the proper dilution factor for each culture is determined, seven samples/culture are prepared. These seven samples are required for the different exposure conditions (Sham, 1, 2, 4, 8, 16, and 32 minutes). Each sample has a total of 10 ml/tube. Each sample is then transferred into sterile Whirl-Pak (registered trademark) bags and sealed, placed into the ultrasonic field and exposed. Each sample has three of its own sham plates (which receive no ultrasonic exposure) to compare to the ultrasound exposed plates.

After exposure, three 0.1 ml plates are prepared for each sample and incubated at 37 degrees Centigrade for 24 hours. After incubation, the colonies that have grown are counted and compared to the results of the control plates.

A total of 39 experiments were conducted on 4 cultures of bacteria, at three meter settings, viz.,

| | |
|---|---|
| *S. aureus:* | 3 experiments at 220 V AC |
| | 6 experiments at 170 V AC |
| | 2 experiments at 110 V AC |
| *P. aeruginosa:* | 3 experiments at 220 V AC |
| | 5 experiments at 170 V AC |
| | 3 experiments at 110 V AC |
| *E. coli:* | 8 experiments at 170 V AC |
| | 3 experiments at 110 V AC |
| *B. subtilis:* | 3 experiments at 170 V AC |
| | 3 experiments at 110 V AC |

The meter settings were related to the ultrasonic exposure intensities as shown in Table 1.

For each meter setting for each bacteria, there were six exposure times (1, 2, 4, 8, 16 and 32 minutes) along with sham exposures. For each experiment, there are six individual plates for each exposure condition, 3 for shams and 3 for exposed. These plate counts are then averaged and computed into formula 1 to determine the cell concentration and to develop the graph of percent killed relative to the control.

3. Results

The results are shown in Tables 2–5. There is a clear trend of greater kill as the exposure time is increased. There is also a difference in the kill rate as a function of bacteria type.

The most difficult bacteria to kill appears to be *E. coli* and the easiest to kill is *B. subtilis*.

Evaluating the two bacteria, *S. aureus* and *P. aeruginosa*, for which there are data at all three meter settings suggests the following. A much greater ultrasonic intensity would be required to kill substantially all of the *S. aureus* than that for *P. aeruginosa*. It appears that the kill rate is about one-half to one-third for *S. aureus* as compared with *P. aeruginosa*. Given the fact that extrapolating outside of the available data range is subject to many problems, it would appear that a doubling of the intensity from the 220 V AX meter setting for *P. aeruginosa* might substantially kill most of this bacteria. Therefore, based upon energy considerations, an addition two to three times in intensity would be required for substantial kill of *S. aureus*.

EXAMPLE 3

1. Types

*Feline herpesvirus* type 1 (FVH-1)
*Feline calicivirus*

2. Procedure

Two analytical procedures were employed to determine the effect of an ultrasonic field on virus viability (survival), viz., infectivity and structural integrity.

Ten-fold dilutions of the source viruses are made in maintenance media. A dilution is then transferred into 2 sterile Whirl-Pak (registered trademark) bags (10 ml/bag), one exposed or treated sample and one control or unexposed sample. The samples are kept at 4 degrees Centigrade before and after ultrasound exposure. Controls are kept at the same temperature (39 degrees Centigrade) a the exposed samples for the duration of the treatment.

TABLE 2

| | Percentage Killed S. aureus | | |
|---|---|---|---|
| Exposure Time | 220 V | 170 V | 110 V |
| 32 minutes | 54.8% | 48.6% | 18.0% |
| 16 minutes | 11.1% | 37.4% | 11.7% |
| 8 minutes | 30.0% | 26.3% | 19.3% |
| 4 minutes | 9.4% | 28.3% | 15.7% |
| 2 minutes | 25.0% | 27.7% | 13.0% |
| 1 minute | 28.6% | 28.8% | 26.4% |

220 V setting 3 experiments
170 V setting 6 experiments
110 V setting 2 experiments

TABLE 3

| | Percentage Killed P. aeruginosa | | |
|---|---|---|---|
| Exposure Time | 220 V | 170 V | 110 V |
| 32 minutes | 90.0% | 61.4% | 66.7% |
| 16 minutes | 84.5% | 59.9% | 42.6% |
| 8 minutes | 60.4% | 39.4% | 22.4% |
| 4 minutes | 66.7% | 38.8% | 15.0% |
| 2 minutes | 73.0% | 54.1% | 33.8% |
| 1 minute | 84.4% | 17.2% | 14.4% |

220 V setting 3 experiments
170 V setting 5 experiments
110 V setting 3 experiments

TABLE 4

| | Percentage Killed E. coli | | |
|---|---|---|---|
| Exposure Time | 220 V | 170 V | 110 V |
| 32 minutes | N | 32.7% | 40.0% |
| 16 minutes | O | 19.6% | 8.9% |
| 8 minutes | D | 13.9% | 24.0% |
| 4 minutes | A | 25.3% | 7.7% |
| 2 minutes | T | 15.2% | 19.6% |
| 1 minute | A | 21.8% | 18.2% |

220 V setting 0 experiments
170 V setting 8 experiments
110 V setting 3 experiments

TABLE 5

| | Percentage Killed B. subtilis | | |
|---|---|---|---|
| Exposure Time | 220 V | 170 V | 110 V |
| 32 minutes | N | 76.1% | 8.8% |
| 16 minutes | O | 78.1% | 6.1% |
| 8 minutes | D | 73.1% | 17.7% |
| 4 minutes | A | 59.0% | 11.3% |
| 2 minutes | T | 40.2% | 0.0% |
| 1 minute | A | 36.3% | 0.0% |

220 V setting 0 experiments
170 V setting 3 experiments
110 V setting 3 experiments The amount (titer) of the infectious virus in a sample prior to and after treatment (ultrasound exposure) is measured by a virus microtitration procedure for $TCID_{50}$ (50 percent tissue culture infectious dose) end point determination. After exposure, logarithmic dilutions of each exposed and control sample as well as the original sample dilution (back titration) are made in maintenance media. Each dilution is then added in an appropriate volume to 4 wells of a 96-well cell culture plate.

The inoculated cultures are incubated 37 degrees Centigrade in a 5 percent $CO_2$ atmosphere environment for five days. If the cells in the inoculated well show a specific viral cytopathic effect (CPE), then it is considered positive (infected). The end point is determined from the highest dilution which produced a CPE in 50 percent of the cell cultures inoculated based on the calculation method of Reed and Muench (Am. J. Hygiene 27(3): 493–497, 1938).

The structural integrity of ultrasonic exposed virus compared to nonexposed virus is evaluated by imaging the virus with negative staining electron microscopy. The threshold of detection for virus by this procedure is a final virus titer in the sample of greater than $10^4$ $TCID_{50}$/ml. Virus from 5 ml of each sample is pelleted by ultracentrifugation. The virus particles in the pellet are then suspended in distilled water, an aliquot of which is stained with 1 percent phosphotungstic acid and placed on Forvar carbon-coated grids.

The criterion used to group viruses into families are the nature of the genome (DNA or RNA, double or single strand, segmented or nonsegmented), the biochemical characteristics (such as viral specified enzymes), and the morphology of the viron (the original classification scheme). Physical disruption of the virion structure (morphology) abrogates viral infectivity. The primary focus of this section of the study is to determine the effect of an ultrasonic field on viral viability as measured by viral infectivity.

Because of this focus, viruses used were chosen based on their morphology, enveloped or nonenveloped, and to represent a viral family that either contains or has similar structure to a human virus of interest. The particular viruses chosen were *Feline herpesvirus* which is of the same subfamily as human herpes simplex virus type 1 and 2 and *Feline calicivirus* which has similar morphology to the Picornaviridae family which contains human enteric viruses (i.e., poliovirus). Human viruses can be used once successful viral inactivation ultrasonic parameters are established.

3. Results

The results are shown in Table 6.

Virus Results

A total of 18 virus experiments have been performed, twelve with feline herpesvirus type 1 (FHV) and six with the feline calicivirus (FCV). The virus was titered and put into sterile Whirl-Pak (registered trademark) bags then transported at 4 degrees Centigrade to the tub.

For experiments 1–5 (Tables 6–10), there were two exposure times (30 and 60 minutes), both at a meter setting of 170 V AC for FHV. For experiments 6–12 (Tables 11–17), there was one exposure condition (60 minutes at a meter setting of 170 V AC) for FHV. For experiments 13–16 (Tables 18–21), there was one exposure condition (60 minutes at a meter setting of 170 V AC) and for experiments 17–18 (Tables 22 and 23), also one exposure condition (60 minutes at a meter setting of 220 V AC), for FCV. All experiments included appropriate controls (called back titration) and sham (virus placed in bath without being exposed to sound).

For the first two experiments, the virus was analyzed for both structural integrity and infectivity. It was concluded that the structural integrity analysis did not provide useful information and thus was not included for subsequent experiments where only infectivity analysis was performed.

Viral Structural Integrity

Negative staining electron microscopy was used to visualize the virions in the treated, sham and back titration samples for Experiments 1 and 2 (enveloped virus). Significant differences were not apparent. This result may in part be due to an aggregation phenomenon that occurs at virus titers necessary for the limits of detection by this technique, that is, a titer $10^4$ to $10^5$ $TCID_{50}/ml$ (see Viral Infectivity, Experiments 1-6 for discussion of the aggregation phenomenon problem).

TABLE 6

| Sample | | | Titer ($TCID_{50}/ml$) | Negative Staining EM* |
|---|---|---|---|---|
| 1. Backtitration | | | $2.4 \times 10^4$ | No virus seen |
| 2. FHV 30/exp. | | 39 degrees C. | $7.2 \times 10^2$ | No virus seen |
| 3. FHV 30/sham | | 39 degrees C. | $2.2 \times 10^4$ | No virus seen |
| 4. FHV 60/exp. | | 39 degrees C. | $2.2 \times 10^1$ | No virus seen |
| 5. 60/sham | | 39 degrees C. | $1.3 \times 10^4$ | No virus seen |

*Limits of detection by negative staining EM fall in the range of $10^4$ to $10^5$ $TCID_{50}/ml$.

TABLE 7

Experiment 2
10 ml/bag
Titer used: $10^6$ $TCID_{50}/ml$

| Sample | | | Titer ($TCID_{50}/ml$) | Negative Staining EM* |
|---|---|---|---|---|
| 1. Back titration | | | $7.2 \times 10^5$ | Virus and nucleocapsid seen |
| 2. FHV 30/exp. | | 39 degrees C. | $7.2 \times 10^5$ | Virus and nucleocapsid seen |
| 3. FHV 30/sham | | 39 degrees C. | $4 \times 10^5$ | Virus and nucleocapsid seen |
| 4. FHV 60/exp. | | 39 degrees C. | $4 \times 10^5$ | Virus and nucleocapsid seen |
| 5. FHV 60/sham | | 39 degrees C. | $7.2 \times 10^5$ | Virus and nucleocapsid seen |

*Limits of detection by negative staining EM fall in the range of $10^4$ to $10^5$ $TCID_{50}/ml$.

TABLE 8

Experiment 3
10 ml/bag
Titer used: $10^6$ ($TCID_{50}/ml$)

| | | | Titer ($TCID_{50}/ml$) |
|---|---|---|---|
| 1. Back titration | | | $2.6 \times 10^5$ |
| 2. FHV 30/exp. | | 39 degrees C. | $4.0 \times 10^5$ |
| 3. FHV 30/sham | | 39 degrees C. | $4.0 \times 10^5$ |
| 4. FHV 60/exp. | | 39 degrees C. | $2.2 \times 10^5$ |
| 5. FHV 60/sham | | 39 degrees C. | $2.2 \times 10^5$ |

TABLE 9

Experiment 4
10 ml/bag
Titer used: $10^4$ and $10^5$ $TCID_{50}/ml$

| | | | Titer ($TCID_{50}/ml$) |
|---|---|---|---|
| $10^5$ | | | |
| 1. Back titration | | | $4.7 \times 10^5$ |
| 2. FHV 30/exp. | | 39 degrees C. | $2.2 \times 10^5$ |
| 3. FHV 30/sham | | 39 degrees C. | $4.0 \times 10^5$ |
| 4. FHV 60/exp. | | 39 degrees C. | $2.2 \times 10^5$ |
| 5. FHV 60/sham | | 39 degrees C. | $4.0 \times 10^5$ |
| $10^4$ | | | |
| 6. Back titration | | | $4.0 \times 10^4$ |
| 7. FHV 30/exp. | | 39 degrees C. | $4.0 \times 10^4$ |
| 8. FHV 30/sham | | 39 degrees C. | $2.2 \times 10^4$ |
| 9. FHV 60/exp. | | 39 degrees C. | $2.2 \times 10^1$ |
| 10. FHV 60/sham | | 39 degrees C. | $2.2 \times 10^4$ |

TABLE 10

Experiment 5
10 ml/bag
Titer used: $10^4$ and $10^5$ $TCID_{50}/ml$

| | | | Titer ($TCID_{50}/ml$) |
|---|---|---|---|
| $10^5$ | | | |
| 1. Back titration | | | $5.6 \times 10^4$ |
| 2. FHV 30/exp. | | 39 degrees C. | $1.3 \times 10^5$ |
| 3. FHV 30/sham | | 39 degrees C. | $1.3 \times 10^5$ |
| 4. FHV 60/exp. | | 39 degrees C. | $2.2 \times 10^5$ |
| 5. FHV 60/sham | | 39 degrees C. | $7.2 \times 10^4$ |
| $10^4$ | | | |
| 6. Back titration | | | $1.2 \times 10^5$ |
| 7. FHV 30/exp. | | 39 degrees C. | $2.2 \times 10^3$ |
| 8. FHV 30/sham | | 39 degrees C. | $7.2 \times 10^3$ |
| 9. FHV 60/exp. | | 39 degrees C. | 0 |
| 10. FHV 60/sham | | 39 degrees C. | $4.0 \times 10^4$ |

TABLE 11

Experiment 6
10 ml/bag
A = sonicated source virus*
B = nonsonicated source virus*
Titer used: $10^5$ and $10^4$ $TCID_{50}/ml$

| | | | Titer ($TCID_{50}/ml$) |
|---|---|---|---|
| A $10^5$ | | | |
| 1. Back titration | | | $4.0 \times 10^5$ |
| 2. FHV 60/exp. | | 39 degrees C. | $7.2 \times 10^5$ |
| 3. FHV 60/sham | | 39 degrees C. | $7.2 \times 10^5$ |
| B $10^5$ | | | |
| 4. Back titration | | | $4.0 \times 10^5$ |
| 5. FHV 60/exp. | | 39 degrees C. | $2.2 \times 10^5$ |
| 6. FHV 60/sham | | 39 degrees C. | $4.0 \times 10^5$ |
| A $10^4$ | | | |
| 7. Back titration | | | $2.2 \times 10^5$ |
| 8. FHV 60/exp. | | 39 degrees C. | $4.0 \times 10^2$ |
| 9. FHV 60/sham | | 39 degrees C. | $7.2 \times 10^4$ |
| B $10^4$ | | | |
| 10. Back titration | | | $7.2 \times 10^4$ |
| 11. FHV 60/exp. | | 39 degrees C. | $7.2 \times 10^1$ |
| 12. FHV 60/sham | | 39 degrees C. | $1.3 \times 10^2$ |

*The sonication referred to here is not from the 26 kHz source of the tub. This sonication was for the purpose of studying the aggregation phenomena. This sonication did not affect the aggregation phenomena.

TABLE 12

Experiment 7
10 ml/bag
All sonications done for 60 minutes at 39 degrees Centigrade

| | Titer ($TCID_{50}/ml$) |
|---|---|
| $10^5$ | |
| 1. Back titration | $7.2 \times 10^5$ |
| 2. FHV exp. | $4.0 \times 10^5$ |
| 3. FHV sham | $1.28 \times 10^6$ |
| $10^4$ | |
| 4. Back titration | $2.24 \times 10^5$ |
| 5. FHV exp. | $2.24 \times 10^4$ |
| 6. FHV sham | $4.0 \times 10^4$ |
| $10^3$ | |
| 7. Backtitration | $7.2 \times 10^3$ |
| 8. FHV exp. | $2.24 \times 10^3$ |
| 9. FHV sham | $2.24 \times 10^3$ |
| $10^2$ | |
| 10. Back titration | $4.0 \times 10^2$ |
| 11. FHV exp. | 0 |
| 12. FHV sham | $4.0 \times 10^2$ |

TABLE 13

Experiment 8
10 ml/bag
All sonications done for 60 minutes at 39 degrees Centigrade

| | Titer ($TCID_{50}/ml$) |
|---|---|
| $10^5$ | |

TABLE 13-continued

Experiment 8
10 ml/bag
All sonications done for 60 minutes at 39 degrees Centigrade

| | | Titer (TCID$_{50}$/ml) |
|---|---|---|
| 1. | Back titration | $1.28 \times 10^6$ |
| 2. | FHV exp. | $4.0 \times 10^5$ |
| 3. | FHV sham | $2.24 \times 10^5$ |
| $10^4$ | | |
| 4. | Back titration | $1.28 \times 10^5$ |
| 5. | FHV exp. | $1.28 \times 10^3$ |
| 6. | FHV sham | $1.28 \times 10^4$ |
| $10^3$ | | |
| 7. | Back titration | $2.24 \times 10^4$ |
| 8. | FHV exp. | 0 |
| 9. | FHV sham | $2.24 \times 10^3$ |

TABLE 14

Experiment 9
10 ml/bag
All sonications done for 60 minutes at 39 degrees Centigrade

| | | Titer (TCID$_{50}$/ml) |
|---|---|---|
| $10^4$ | | |
| 1. | Back titration | $7.2 \times 10^4$ |
| 2. | FHV exp. | 0 |
| 3. | FHV sham | $1.28 \times 10^4$ |
| $10^3$ | | |
| 4. | Back titration | $7.2 \times 10^3$ |
| 5. | FHV exp. | $2.2 \times 10^1$ |
| 6. | FHV sham | $2.24 \times 10^3$ |
| $10^2$ | | |
| 7. | Back titration | $7.2 \times 10^2$ |
| 8. | FHV exp. | $2.2 \times 10^1$ |
| 9. | Sham | $2.24 \times 10^2$ |

TABLE 15

Experiment 10
10 ml/bag
All sonications done for 60 minutes at 39 degrees Centigrade

| | | Titer (TCID$_{50}$/ml) |
|---|---|---|
| $10^4$ | | |
| 1. | Back titration | $4.0 \times 10^3$ |
| 2. | FHV exp. | $4.0 \times 10^3$ |
| 3. | FHV sham | $7.2 \times 10^3$ |
| $10^3$ | | |
| 4. | Back titration | $1.28 \times 10^2$ |
| 5. | FHV exp. | 0 |
| 6. | FHV sham | $2.24 \times 10^3$ |
| $10^2$ | | |
| 7. | Back titration | 0 |
| 8. | FHV exp. | 0 |
| 9. | FHV sham | 0 |

TABLE 16

Experiment 11
10 ml/bag
All sonications done for 60 minutes at 39 degrees Centigrade

| | | Titer (TCID$_{50}$/ml) |
|---|---|---|
| $10^4$ | | |
| 1. | Back titration | $7.2 \times 10^4$ |
| 2. | FHV exp. | $2.24 \times 10^4$ |
| 3. | FHV sham | $2.24 \times 10^4$ |
| $10^3$ | | |
| 4. | Back titration | $7.2 \times 10^2$ |
| 5. | FHV exp. | 0 |
| 6. | FHV sham | $7.2 \times 10^2$ |
| $10^2$ | | |
| 7. | Back titration | $4.0 \times 10^2$ |
| 8. | FHV exp. | 0 |
| 9. | FHV sham | 0 |

TABLE 17

Experiment 12
10 ml/bag
All sonications done for 60 minutes at 39 degrees Centigrade

| | | Titer (TCID$_{50}$/ml) |
|---|---|---|
| $10^4$ | | |
| 1. | Back titration | $2.24 \times 10^4$ |
| 2. | FHV exp. | 0 |
| 3. | FHV sham | $1.28 \times 10^4$ |
| $10^3$ | | |
| 4. | Back titration | $4.0 \times 10^2$ |
| 5. | FHV exp. | 0 |
| 6. | FHV sham | $7.2 \times 10^2$ |
| 7. | Back titration | $7.2 \times 10^1$ |
| 8. | FHV exp. | 0 |
| 9. | FHV sham | 0 |

TABLE 18

Experiment 13
10 ml/bag
All sonications done for 60 minutes at 39 degrees Centigrade

| | | Titer (TCID$_{50}$/ml) |
|---|---|---|
| $10^5$ | | |
| 1. | Back titration | $4.0 \times 10^4$ |
| 2. | FCV exp. | $7.2 \times 10^3$ |
| 3. | FCV sham | $1.28 \times 10^4$ |
| $10^4$ | | |
| 4. | Back titration | $2.24 \times 10^3$ |
| 5. | FCV exp. | $4.0 \times 10^2$ |
| 6. | FCV sham | $7.2 \times 10^2$ |
| $10^3$ | | |
| 7. | Back titration | $2.24 \times 10^2$ |
| 8. | FCV exp. | $2.24 \times 10^1$ |
| 9. | FCV sham | $7.2 \times 10^1$ |
| $10^2$ | | |
| 10. | Back titration | 0 |
| 11. | FCV exp. | 0 |
| 12. | FCV sham | 0 |

TABLE 19

Experiment 14
10 ml/bag
All sonications done for 60 minutes at 39 degrees Centigrade

| | | Titer (TCID$_{50}$/ml) |
|---|---|---|
| $10^5$ | | |
| 1. | Back titration | $1.28 \times 10^5$ |
| 2. | FCV exp. | $1.28 \times 10^5$ |
| 3. | FCV sham | $4.0 \times 10^4$ |
| $10^4$ | | |
| 4. | Back titration | $2.24 \times 10^4$ |
| 5. | FCV exp. | $7.2 \times 10^3$ |
| 6. | FCV sham | $4.0 \times 10^3$ |
| $10^3$ | | |
| 7. | Back titration | $2.24 \times 10^3$ |
| 8. | FCV exp. | $1.28 \times 10^2$ |
| 9. | FCV sham | $1.28 \times 10^2$ |
| $10^2$ | | |
| 10. | Back titration | $4.0 \times 10^2$ |
| 11. | FCV exp. | $2.24 \times 10^1$ |
| 12. | FCV sham | 0 |

TABLE 20

Experiment 15
10 ml/bag
All sonications done for 60 minutes at 39 degrees Centigrade

| | | Titer (TCID$_{50}$/ml) |
|---|---|---|
| $10^5$ | | |
| 1. | Back titration | $4.0 \times 10^5$ |
| 2. | FCV exp. | $1.28 \times 10^4$ |
| 3. | FCV sham | $7.2 \times 10^4$ |
| $10^4$ | | |

TABLE 20-continued

Experiment 15
10 ml/bag
All sonications done for 60 minutes at 39 degrees Centigrade

| | Titer (TCID$_{50}$/ml) |
|---|---|
| 4. Back titration | $4.0 \times 10^4$ |
| 5. FCV exp. | $2.24 \times 10^3$ |
| 6. FCV sham | $1.28 \times 10^4$ |
| $10^3$ | |
| 7. Back titration | $1.28 \times 10^3$ |
| 8. FCV exp. | $2.24 \times 10^2$ |
| 9. FCV sham | $2.24 \times 10^2$ |
| $10^2$ | |
| 10. Back titration | $4.0 \times 10^2$ |
| 11. FCV exp. | $7.2 \times 10^1$ |
| 12. FCV sham | $2.24 \times 10^1$ |

TABLE 21

Experiment 16
10 ml/bag
All sonications done for 60 minutes at 39 degrees Centigrade

| | Titer (TCID$_{50}$/ml) |
|---|---|
| $10^5$ | |
| 1. Back titration | $1.28 \times 10^5$ |
| 2. FCV exp. | $7.2 \times 10^4$ |
| 3. FCV sham | $7.2 \times 10^4$ |
| $10^4$ | |
| 4. Back titration | $7.2 \times 10^3$ |
| 5. FCV exp. | $4.0 \times 10^3$ |
| 6. FCV sham | $1.28 \times 10^4$ |
| $10^3$ | |
| 7. Back titration | $1.28 \times 10^3$ |
| 8. FCV exp. | 0 |
| 9. FCV sham | $4.0 \times 10^2$ |
| $10^2$ | |
| 10. Back titration | $2.24 \times 10^2$ |
| 11. FCV exp. | 0 |
| 12. FCV sham | $4.0 \times 10^1$ |

TABLE 22

Experiment 17
10 ml/bag
All sonications done for 60 minutes at 39 degrees Centigrade

| | Titer (TCID$_{50}$/ml) |
|---|---|
| 1. Back titration | $7.2 \times 10^5$ |
| 2. FCV exp. | $1.28 \times 10^5$ |
| 3. FCV sham | $2.24 \times 10^5$ |
| $10^4$ | |
| 4. Back titration | $2.24 \times 10^4$ |
| 5. FCV exp. | $7.2 \times 10^3$ |
| 6. FCV sham | $2.24 \times 10^4$ |
| $10^3$ | |
| 7. Back titration | $4.0 \times 10^3$ |
| 8. FCV exp. | $1.28 \times 10^2$ |
| 9. FCV sham | $2.24 \times 10^3$ |
| $10^2$ | |
| 10. Backtitration | $2.24 \times 10^2$ |
| 11. FCV exp. | $4.0 \times 10^1$ |
| 12. FCV sham | $4.0 \times 10^2$ |

TABLE 23

Experiment 18
10 ml/bag
All sonications done for 60 minutes at 39 degrees Centigrade

| | Titer (TCID$_{50}$/ml) |
|---|---|
| 1. Back titration | $1.28 \times 10^6$ |
| 2. FCV exp. | $4.0 \times 10^4$ |
| 3. FCV sham | $4.0 \times 10^5$ |
| $10^4$ | |
| 4. Back titration | $1.28 \times 10^5$ |
| 5. FCV exp. | $7.2 \times 10^3$ |
| 6. FCV sham | $7.2 \times 10^4$ |

TABLE 23-continued

Experiment 18
10 ml/bag
All sonications done for 60 minutes at 39 degrees Centigrade

| | Titer (TCID$_{50}$/ml) |
|---|---|
| $10^3$ | |
| 7. Back titration | $7.2 \times 10^3$ |
| 8. FCV exp. | $2.24 \times 10^3$ |
| 9. FCV sham | $7.2 \times 10^2$ |
| $10^2$ | |
| 10. Back titration | $7.2 \times 10^2$ |
| 11. FCV exp. | $1.28 \times 10^2$ |
| 12. FCV sham | $1.28 \times 10^2$ |

Viral Infectivity

Enveloped Virus (FHV-1)

1. Experiments 1-6

A titer of $10^5$ TCIV$_{50}$/ml appeared to be the critical infectious unit number at which viral aggregation is most evident. Such a viral aggregate is measured as one infectious unit. This aggregation phenomenon protects the more internal virions from the inactivating effects of the ultrasound. Therefore, since all virions within an aggregate must be inactivated to destroy the infectivity of an aggregate, the virus titer was not measurably reduced by treatment. Therefore, subsequent experiments used titers less than or equal to $10^5$ TCID$_{50}$/ml.

2. Experiments 7-12 (FHV)

The ultrasonic exposure conditions used (170 V AC meter setting for 60 minutes at 39 degrees Centigrade) resulted in significant reduction of infectivity of samples containing a titer $10^4$ TCID$_{50}$/ml. Virions in samples containing titer of $10^2$ TCID$_{50}$/ml were more liable to environmental conditions (such as temperature and light), therefore, were easily inactivated.

3. Experiment 13-16 (FCV)

The ultrasonic exposure conditions were the same as for experiments 7-12. Results indicate that such conditions did not significantly reduce viral infectivity.

4. Experiment 17 and 18 (FCV)

The higher ultrasonic exposure conditions (220 V AC meter setting for 60 minutes) showed that the virus was not significantly reduced.

CONCLUSION

The experimental conditions used significantly reduced viral infectivity of the lower titered enveloped virus (FHF) samples. However, the nonenveloped virus (FCV) was refractive to the inactivating effects of the ultrasound. This reflects the fact that enveloped viruses are more liable to environmental influences than are nonenveloped viruses.

The enveloped virus consists of a lipid/protein bilayer membrane (the envelope). Disruption of the envelope generally kills this virus type. To kill the nonenveloped type virus (FCV) requires disruption or destruction of the nucleocapsid. More energy is required to destroy the nucleocapsid than disrupt the envelope. The findings herein are consistent with this observation.

The experiments indicate the ability of 30 KHz ultrasound to destroy microbes in amounts related to the time of radiation and intensity of the ultrasound. This indicates the ability to sterilize with or without additives. The killing intensity can be obtained by increasing power until samples in bags are completely destroyed.

From the above description, it can be understood that the apparatus and method of this invention has several advantages over the prior art, such as: (1) it has hygienic, therapeutic and antimicrobial benefits while being harmless to animals; (2) it makes economical use of vibrating transducers by avoiding standing waves and using low attenuation water as a working fluid; and (3) performs both cleaning and healing benefits while at the same time provide antiviral, antibacterial and antifungal activity in a manner making it suitable for treatment of certain particularly severe maladies such as treating patients with severe burns.

Although a preferred embodiment of the invention has been described with some particularity, many modifications and variations in the invention are possible within the light of the above teachings. Therefore, it is to be understood, that within the scope of the appended claims, the invention may be practiced other than as specifically described.

What is claimed is:

1. A method of treating animals in a working fluid contained within wall means comprising the steps of:
   immersing a body portion of the animal into the working fluid during a time period with the body portion being in acoustic contact with the fluid; and
   applying ultrasonic waves through the working fluid to the body portion at a frequency in the range of 15 kilohertz to 500 kilohertz and a power density that is not irritating to the animal during the time period; and
   reducing thermal layering during the application of ultrasonic waves through the working fluid.

2. A method in accordance with claim 1 in which thermal layering is reduced by adding a surfactant having a low enough density to avoid attenuation of sound significantly across the length of a tub hot reducing thermal layering and bubbles within the tub.

3. A method of treating animals in a working fluid contained within wall means comprising the steps of:
   immersing a body portion of the animal into the working fluid during a time period with the body portion being in acoustic contact with the fluid; and
   applying ultrasonic waves through the working fluid to the body portion at a frequency in the range of 15 kilohertz to 500 kilohertz and a power density that is not irritating to the animal during the time period; and
   the step of applying ultrasonic waves including the step of applying ultrasonic waves which form stable cavitation without transient cavitation.

4. A method in accordance with claim 3 in which instability leading to transient cavitation is avoided by transmitting asymmetrical ultrasonic pulses.

5. A method of treating animals in a working fluid contained within wall means comprising the steps of:
   immersing a body portion of the animal into the working fluid during a time period with the body portion being in acoustic contact with the fluid; and
   applying ultrasonic waves through the working fluid to the body portion at a frequency in the range of 15 kilohertz to 500 kilohertz and a power density that is not irritating to the animal during the time period;
   the step of applying ultrasonic waves including the step of applying ultrasonic waves including the step of inserting an ultrasonic vibrator within the working fluid and moving it to a position appropriate for cleaning action.

6. A method in accordance with claim 5 in which the step of inserting comprises the step of attaching the ultrasonic vibrator to a tub in a position in which the vibrator may be moved within the liquid of the tub.

7. A method of treating animals in a working fluid contained within wall means comprising the steps of:
   immersing a body portion of the animal into the working fluid during a time period with the body portion being in acoustic contact with the fluid; and
   applying ultrasonic waves through the working fluid to the body portion at a frequency in the range of 15 kilohertz to 500 kilohertz and a power density that is not irritating to the animal during the time period;
   absorbing a portion of said ultrasonic waves in plastic wall means whereby the transmission to air of said ultrasonic waves is reduced.

8. A method of treating animals in a working fluid contained within wall means comprising the steps of:
   immersing a body portion of the animal into the working fluid during a time period with the body portion being in acoustic contact with the fluid; and
   applying ultrasonic waves through the working fluid to the body portion at a frequency in the range of 15 kilohertz to 500 kilohertz and a power density that is not irritating to the animal during the time period;
   the step of immersing a body portion of an animal including the step of immersing a body portion of an animal into at least partly degassed water.

9. A method of treating animals in a working fluid contained within wall means comprising the steps of:
   immersing a body portion of the animal into the working fluid during a time period with the body portion being in acoustic contact with the fluid; and
   applying ultrasonic waves through the working fluid to the body portion at a frequency in the range of 15 kilohertz to 500 kilohertz and a power density that is not irritating to the animal during the time period;
   the step of immersing a body portion of an animal including the step of immersing a body portion of an animal into water in which an additive capable of aiding in at least one of cleaning and antimicrobial action is included.

10. A method of treating animals in a working fluid contained within wall means comprising the steps of:
    immersing a body portion of the animal into the working fluid during a time period with the body portion being in acoustic contact with the fluid; and
    applying ultrasonic waves through the working fluid to the body portion at a frequency in the range of 15 kilohertz to 500 kilohertz and a power density that is not irritating to the animal during the time period; and
    detecting ultrasound in said working fluid and providing an indication of the power density.

11. A method of treating animals in a working fluid contained within wall means comprising the steps of:

immersing a body portion of the animal into the working fluid during a time period with the body portion being in acoustic contact with the fluid; and applying ultrasonic waves through the working fluid to the body portion at a frequency in the range of 15 kilohertz to 500 kilohertz and a power density that is not irritating to the animal during the time period; and reducing the transmission of said ultrasonic waves through said working fluid upon detecting the insertion of a foreign body in said working fluid.

12. A method of treating animals comprising the steps of:
   immersing a body portion of the animal into a working fluid with the body portion being in acoustic contact with the fluid;
   applying ultrasonic waves through the working fluid to the body portion at a frequency in the range of 15 kilohertz to 500 kilohertz and a power density in the range of 0.1 to 5 watts per square centimeter through the working fluid for a time less than 15 minutes and at a power and frequency that does not cause transient cavitation; and
   reducing thermal layering in the working fluid by the addition of a surfactant and utilizing at least partly degassed water.

13. A method in accordance with claim 12 in which the water is degassed by creating vacuum pressure and impacting the water against a hard surface within one minute after being first exposed to the vacuum pressure.

14. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz; and
   means for moving ultrasonic transducers within the working fluid to aim and position an ultrasonic radiating head.

15. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz;
   means for moving ultrasonic transducers within the working fluid to aim and position an ultrasonic radiating head with said means for applying, said means for applying includes bracket means for mounting a movable holder for a transducer to the container means at one point; said means for moving including an adjustable means whereby the transducer may be lowered or raised or changed in angular position within the fluid.

16. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz; and
   means for degassing fluid as it is applied to the container means.

17. Apparatus in accordance with claim 16 in which said means for degassing includes a means for depressurizing the working fluid and impacting it upon a surface within one minute of depressurizing.

18. Apparatus in accordance with claim 17 in which said means for depressurizing includes a faucet means having a reduced cross section portion whereby the velocity of the working fluid is increased and an expanded cross section portion whereby high velocity liquid is exposed suddenly to a larger area, whereby it may be impacted upon a hard surface within one minute.

19. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz;
   the container means being sound absorbant plastic.

20. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz;
   wherein the means for applying ultrasonic waves includes means for preventing cavitation from being transient by causing the ultrasonic waves to be asymmetrical in pressure.

21. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz;
   said means for applying ultrasonic waves comprises a plurality of transducers each mounted to a wall of the container means by gasket means whereby a coupling between the plurality of transducer means and the working fluid is reduced.

22. Apparatus for ultrasonic treatment of animals comprising:
   container means adapted to contain a working fluid in which at least a portion of an animal may be immersed for treatment by ultrasonic waves; and
   means for applying ultrasonic waves through the working fluid within the container means in a power density range of less than 15 watts per square centimeter and a frequency range between 15 kilohertz and 500 kilohertz; and at least one of the container means and the means for applying ultrasonic waves through the working fluid including a material which absorbs sound of the frequency used.

23. Apparatus for ultrasonic treatment of animals comprising:

container means adapted to contain a working fluid in which at least a portion of an animal may be immersed for treatment by ultrasonic waves; and means for applying ultrasonic waves through the working fluid within the container means in a power density range of less than 15 watts per square centimeter and a frequency range between 15 kilohertz and 500 kilohertz; and a degasser adapted to remove at least some gas from water and positioned to fill the container means with at least partly degassed water.

24. Apparatus for ultrasonic treatment of animals comprising:

container means adapted to contain a working fluid in which at least a portion of an animal may be immersed for treatment by ultrasonic waves; and means for applying ultrasonic waves through the working fluid within the container means in a power density range of less than 15 watts per square centimeter and a frequency range between 15 kilohertz and 500 kilohertz; and probe means for sensing power intensity of said ultrasonic waves in said working fluid.

25. Apparatus according to claim 24 further including means for reducing the power emitted by said means for applying ultrasonic waves when the power density measured by said probe means exceeds a predetermined value.

26. Apparatus according to claim 25 further including:

means for sensing the intrusion of an object into said working fluid; and means for reducing the power transmitted by said means for applying ultrasonic waves upon sensing the intrusion of an object into said working fluid.

27. Apparatus for ultrasonic treatment of animals comprising:

container means adapted to contain a working fluid in which at least a portion of an animal may be immersed for treatment by ultrasonic waves;

means for applying ultrasonic waves in a first frequency in a first frequency range of between 15 kilohertz and 500 kilohertz through the working fluid within the container means with a power density which is capable of beneficial effects without being harmful to the animal; and means for modulating the first frequency of the ultrasonic waves with a second sweep frequency across a second frequency band centered on the first frequency.

28. Apparatus in accordance with claim 27 further including means for moving ultrasonic transducers within the working fluid to aim and position an ultrasonic radiating head.

29. Apparatus in accordance with claim 28 in which said means for applying includes bracket means for mounting a movable holder for a transducer to the container means at one point; said means for moving including an adjustable means whereby the transducer may be lowered or raised or changed in angular position within the fluid.

30. Apparatus in accordance with claim 27 further including a means for degassing fluid as it is applied to the container means.

31. Apparatus in accordance with claim 30 in which said means for degassing includes a means for depressurizing the liquid and impacting it upon a surface within one minute of depressurizing.

32. Apparatus in accordance with claim 31 in which said means for depressurizing includes a faucet means having a reduced cross section portion whereby the velocity of the working fluid is increased and an expanded cross section portion whereby high velocity liquid is exposed suddenly to a larger area, whereby it may be impacted upon a hard surface within one minute.

33. Apparatus in accordance with claim 27 in which the container means is sound absorbant plastic.

34. A method of treating animals comprising the steps of:

immersing a body portion of the animal into a working fluid with the body portion having a wound in it and being in acoustic contact with the fluid for a number of times between once every two days and four times a day and for a time period selected to avoid increasing inflammation and retarding healing wherein the animal is cleaned while wound healing is aided; and applying ultrasonic waves through the working fluid to the body portion at a frequency in the range of 15 kilohertz to 500 kilohertz and a power density in the range of 0.1 to 5 watts per square centimeter through the working fluid for a time less than 15 minutes and at a power and frequency that does not cause transient cavitation.

35. A method in accordance with claim 34 further including the step of forming and utilizing a container for the working fluid having sound absorbant plastic walls.

36. A method in accordance with claim 34 further including positioning a faucet to fill a tank, said faucet having within it a means for reducing pressure on the working fluid flowing therethrough and a means for impacting said working fluid against a surface within five seconds of the time its pressure is reduced, whereby said liquid is degassed.

37. A method in accordance with claim 36 in which said faucet is formed to having within it a narrowing portion to increase the velocity of said working fluid followed by an expanding portion whereby the pressure on said working fluid is reduced.

38. A method of making ultrasonic apparatus for the treatment of animals comprising the steps of:

mounting at least one transducer in a vibrator housing to form a vibrator; and mounting to a tub the at least one vibrator for applying ultrasonic vibrations to working fluid in the tub wherein the ultrasonic vibrations in the working fluid are in a frequency range of between 15 kilohertz and 500 kilohertz at power densities over a portion of the range of at least between 0.1 and 30 watts per square centimeter at a location in said tub below a level for the working fluid.

39. A method in accordance with claim 38 further including the step of connecting the at least one vibrator to an electrical drive means for generating electrical pulses wherein the at least one transducer is responsive to the electrical drive means, the electrical drive means including means for driving the at least one transducer to create a pressure in a positive direction followed by lower pressure forming cycles in said frequency range of between 15 kilohertz and 500 kilohertz with the lower pressure portion of each cycle and higher pressure portion being unequal so as to prevent instability leading to transient cavitation.

40. A method in accordance with claim 39 further including the step of applying a higher power in said positive portion of the cycle than in said negative portion of the cycle to said electrical drive means.

41. A method in accordance with claim 38 in which a plurality of vibrators are mounted to a tub, each vibrator having a different vibrating plate, each vibrating plate being separated from the wall of the hub by a gasket and adapted to move with minimum transfer of power to the tub wall or to other vibrating plates.

42. A method in accordance with claim 39 in which the step of mounting at least one vibrator includes the step of attaching at least one vibrator to a tub wall by adjustable interconnecting members that permit .pa movement of the vibrator to different positions manually.

* * * * *